(12) United States Patent
Xiao et al.

(10) Patent No.: US 8,993,072 B2
(45) Date of Patent: Mar. 31, 2015

(54) HALOGENATED ORGANOAMINOSILANE PRECURSORS AND METHODS FOR DEPOSITING FILMS COMPRISING SAME

(71) Applicant: Air Products and Chemicals, Inc., Allentown, PA (US)

(72) Inventors: Manchao Xiao, San Diego, CA (US); Xinjian Lei, Vista, CA (US); Mark Leonard O'Neill, San Marcos, CA (US); Bing Han, Beijing (CN); Ronald Martin Pearlstein, San Marcos, CA (US); Haripin Chandra, Vista, CA (US); Heather Regina Bowen, Vista, CA (US); Agnes Derecskei-Kovacs, Macungie, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 75 days.

(21) Appl. No.: 13/622,117

(22) Filed: Sep. 18, 2012

(65) Prior Publication Data

US 2013/0078392 A1 Mar. 28, 2013

Related U.S. Application Data

(60) Provisional application No. 61/539,717, filed on Sep. 27, 2011.

(51) Int. Cl.
| | | |
|---|---|---|
| C07F 7/02 | (2006.01) | |
| H05H 1/24 | (2006.01) | |
| C23C 16/00 | (2006.01) | |
| C07F 7/12 | (2006.01) | |
| C23C 16/40 | (2006.01) | |
| C23C 16/455 | (2006.01) | |
| H01L 21/02 | (2006.01) | |

(52) U.S. Cl.
CPC . *C07F 7/025* (2013.01); *C07F 7/12* (2013.01); *C23C 16/402* (2013.01); *C23C 16/45536* (2013.01); *C23C 16/45553* (2013.01); *H01L 21/02126* (2013.01); *H01L 21/02164* (2013.01); *H01L 21/02219* (2013.01); *H01L 21/0228* (2013.01); *H01L 21/02532* (2013.01); *H01L 21/0262* (2013.01)
USPC . 427/579; 427/578; 427/248.1; 427/255.394; 556/410; 548/406; 546/14; 544/105; 106/287.11

(58) Field of Classification Search
USPC ............ 556/410; 548/406; 546/14; 544/105; 427/248.1, 255.394, 578, 579; 106/287.11
See application file for complete search history.

(56) References Cited

U.S. PATENT DOCUMENTS

| | | |
|---|---|---|
| 6,869,638 B2 | 3/2005 | Baum et al. |
| 7,005,392 B2 | 2/2006 | Baum et al. |
| 7,084,080 B2 | 8/2006 | Borovik et al. |
| 7,332,618 B2 | 2/2008 | Meiere |
| 7,358,194 B2 | 4/2008 | Dip et al. |
| 7,498,273 B2 | 3/2009 | Mallick et al. |
| 7,582,555 B1 | 9/2009 | Lang et al. |
| 7,767,840 B2 | 8/2010 | Shenai-Khatkhate et al. |
| 7,875,312 B2 | 1/2011 | Thridandam et al. |
| 7,875,556 B2 | 1/2011 | Xiao et al. |
| 7,888,233 B1 | 2/2011 | Gauri et al. |
| 7,915,139 B1 | 3/2011 | Lang et al. |
| 7,932,413 B2 | 4/2011 | Xiao et al. |
| 8,164,166 B2 | 4/2012 | Imada et al. |

(Continued)

FOREIGN PATENT DOCUMENTS

| | | |
|---|---|---|
| CS | 267800 | 2/1990 |
| EP | 0 894 802 A2 | 2/1999 |

(Continued)

OTHER PUBLICATIONS

Yoshimoto, A., et al.; "Syntheses of High Molecular Weight Polysilazanes by the Ammonolysis of N,N-Diethylaminosilanes"; Nippon Kagaku Kaishi; vol. 10; 2001; pp. 559-565.

Norbert, A., et al.; "Erzeugung Von SiC-Doppelbindungen in Der Koordinationsspare Von Eisencarbonylkomplexen"; J. Organomet. Chem.; vol. 363; 1989; pp. 7-23.

Washburne, S.S., et al.; "Choloaminosilanes II. Preparation and Spectroscopic Studies on Alkyl-(Dimethylamino) Chlorosilanes"; Journal of Organomettalic Chemistry, Elsevier-Sequoia S.A.; vol. 21, No. 1; Jan. 1, 1970; pp. 59-64.

Emsley, J.; "Aminosliane-Iodosilane Adducts"; Journal of the Chemical Society [Section] A: Inorganic, Physical, Theoretical; 1968.

(Continued)

*Primary Examiner* — Porfirio Nazario Gonzalez
(74) *Attorney, Agent, or Firm* — Rosaleen P. Morris-Oskanian

(57) ABSTRACT

Described herein are precursors and methods of forming films. In one aspect, there is provided a precursor having Formula I:

$$X_m R^1_n H_p Si(NR^2 R^3)_{4-m-n-p} \qquad I$$

wherein X is selected from Cl, Br, I; $R^1$ is selected from linear or branched $C_1$-$C_{10}$ alkyl group, a $C_2$-$C_{12}$ alkenyl group, a $C_2$-$C_{12}$ alkynyl group, a $C_4$-$C_{10}$ cyclic alkyl, and a $C_6$-$C_{10}$ aryl group; $R^2$ is selected from a linear or branched $C_1$-$C_{10}$ alkyl, a $C_3$-$C_{12}$ alkenyl group, a $C_3$-$C_{12}$ alkynyl group, a $C_4$-$C_{10}$ cyclic alkyl group, and a $C_6$-$C_{10}$ aryl group; $R^3$ is selected from a branched $C_3$-$C_{10}$ alkyl group, a $C_3$-$C_{12}$ alkenyl group, a $C_3$-$C_{12}$ alkynyl group, a $C_4$-$C_{10}$ cyclic alkyl group, and a $C_6$-$C_{10}$ aryl group; m is 1 or 2; n is 0, 1, or 2; p is 0, 1 or 2; and m+n+p is less than 4, wherein $R^2$ and $R^3$ are linked or not linked to form a ring.

36 Claims, 1 Drawing Sheet

(56) References Cited

U.S. PATENT DOCUMENTS

| | | |
|---|---|---|
| 2005/0129862 A1 | 6/2005 | Nagaraj et al. |
| 2007/0042570 A1 | 2/2007 | Dip et al. |
| 2008/0207007 A1 | 8/2008 | Thridandam et al. |
| 2009/0104791 A1 | 4/2009 | Nemani et al. |
| 2012/0021127 A1 | 1/2012 | Sato et al. |

FOREIGN PATENT DOCUMENTS

| | | |
|---|---|---|
| EP | 0894802 A2 | 3/1999 |
| JP | 2004308007 | 4/2004 |
| JP | 2009081348 | 4/2009 |
| WO | 02/079211 A1 | 10/2002 |
| WO | 2010106859 | 9/2010 |
| WO | 2011123792 | 10/2011 |
| WO | 2012/167060 A2 | 12/2012 |

OTHER PUBLICATIONS

Anderson, D.G., et al.; "Preparations, Properties and Vibrational Spectra of Some (Dimethylamino) Halogenosilanes"; J. Chem. Soc. Dalton Trans.; 1987; pp. 3029-3034.

Harle, H.D., et al; "Properties and Reactions of Organsilanes and Organogermanes Containing the Potentially Bidentate (X(CH2)n)2N-Group"; Synthesis and Reactivity in Inorganic and Metallorganicchemistry, Marcel Dekker Inc.; vol. 33, No. 10; Jan. 1, 2003; pp. 1825-1834.

H. Breederveld, et al, Substitution of Chlorine in Silicon Tetra-chloride by Dimethylamino, Diethylamino and Piperidino Groups, Laboratory of Chemical Engineering, The University Delft, 1952, 537-539.

D. G. Anderson, et al, Molecular Structures of Some (Dimethylamino)halogenosilanes in the Gas Phase by Electron Diffraction and the Crystal and Molecular Structures of Mono- and Di-chloro(dimethylamino)silane by X-Ray Diffraction at Low Temperatures, J. Chem. Soc., 1987, 3035-3042.

S. S. Washburne, et al, Chloraminosilanes: I. The Preparation of Chloro(dimethylamino)hydrogen Silanes, Inorg. Nucl. Chem. Letters, 1969, 17-19.

R. A. Pike, et al, Preparation of B-Cyanoethyltrichlorosilane Using Silyalmine Catalysts, J. Org. Chem., 1962, 2190-2192.

J. N. Hay, et al, Synthesis of Organic—Inorganic Hybrids via the Non-hydrolytic Sol—Gel Process, Chem. Mater., 2001, 3396-3403.

J. N. Hay, et al, A versatile route to organically-modified silicas and porous silicas via the non-hydrolytic sol-gel process, J. Mater. Chem., 2000, 1811-1818.

V. Passarelli, et al, Aminolysis of the Si—Cl bond and ligand exchange reaction between silicon amido derivatives and SiCl4: synthetic applications and kinetic investigations, The Royal Society of Chemistry, 2003, 413-419.

X. Liu, et al, Chemical vapor deposition of silicon nitride thin films from tris(diethylamino)chlorosilane, Materials Letters, 2005, 11-14.

R. G. Gordon, et al, Silicon Dimethylamido Complexes and Ammonia as Precursors for the Atmospheric Pressure Chemical Vapor Deposition of Silicon Nitride Thin Films, Chem. Mater., 1990, 480-482.

G. Huber, et al, The Molecular Structures of Tetra(amino)silanes, Chem. Ber., 1997, 1167-1174.

J. Chem. Soc. (1909) 95 506.

Washburne. S. S. et al; "Chloraminosilanes II. Preparation and Spectroscopic studies on alky-(dimethylamino) Chlorosilanes," Journal of Organometallic Chemistry; vol. 21, Issue 1; pp. 59-64 (Jan. 1970).

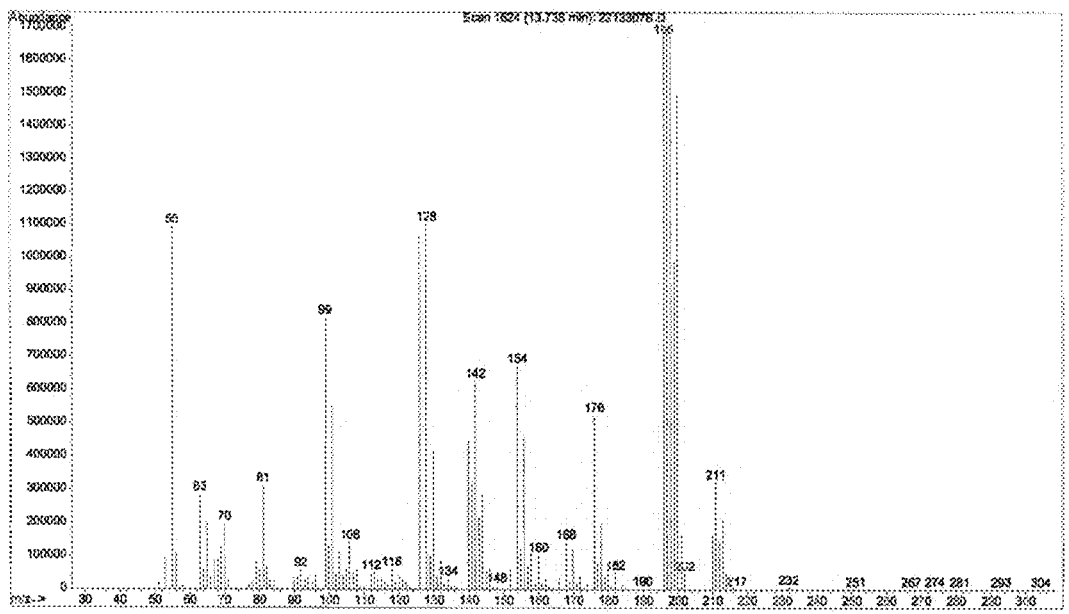

HALOGENATED ORGANOAMINOSILANE PRECURSORS AND METHODS FOR DEPOSITING FILMS COMPRISING SAME

CROSS-REFERENCE TO RELATED APPLICATIONS

This application claims the priority benefit under 35 U.S.C. §119 of the following application: U.S. Provisional Application No. 61/539,717 filed 27 Sep. 2011, the disclosure of which is incorporated herein by reference in its entirety.

BACKGROUND OF THE INVENTION

Precursors, particularly halogenated organoaminosilane precursors that can be used for the deposition of dielectric films, including but not limited to, silicon containing films such as silicon, amorphous silicon, crystalline silicon, microcrystalline silicon, polycrystalline silicon, silicon nitride, silicon oxide, carbon doped silicon oxide, silicon carbo-nitride, and silicon oxynitride films are described herein. In yet another aspect, described herein is the use of the halogenated organoaminosilane precursors for depositing silicon-containing dielectric films in the fabrication of integrated circuit devices. In these or other aspects, the halogenated organoaminosilane precursors may be used for a variety of vapor based deposition processes, including but not limited to, atomic layer deposition ("ALD"), chemical vapor deposition ("CVD"), cyclic chemical vapor deposition ("CCVD"), plasma enhanced chemical vapor deposition ("PECVD"), low pressure chemical vapor deposition ("LPCVD"), and atmospheric pressure chemical vapor deposition ("APCVD") or liquid based deposition processes, including not but not limited to, spin-on, dip coat, aerosol, ink jet, screen printing or spray deposition or film formation methods.

Several classes of compounds can be used as precursors for silicon-containing films such as, but not limited to, silicon oxide or silicon nitride films. Examples of these compounds suitable for use as precursors include silanes, chlorosilanes, polysilazanes, aminosilanes, and azidosilanes. Inert carrier gas or diluents such as, but not limited, helium, hydrogen, nitrogen, etc., are also used to deliver the precursors to the reaction chamber.

U.S. Pat. No. 6,869,638 describes a CVD method of forming gate dielectric thin films such as gate dielectric, high dielectric constant metal oxides, and ferroelectric metal oxides on a substrate using metalloamide compounds and an aminosilane compounds of the following formula: $H_xSiA_y(NR^1R^2)_{4-x-y}$ wherein H is hydrogen; x is from 0 to 3; N is nitrogen; each of $R^1$ and $R^2$ is same or different and is independently selected from the group consisting of H, aryl, perfluoroaryl, $C_1$-$C_8$ alkyl and $C_1$-$C_8$ perfluoroalkyl; and n is from 1-6. Examples of the aminosilane precursors described in the '638 patent include bis(diethylamino)dichlorosilane and tris(diethylamino)chlorosilane.

CWO 2011/123792 describes low temperature, thermal or plasma based ALD methods for forming metal-nitride-containing films from the combination of amino-metal precursors and halogenated metal precursors, preferably forming SiN-containing films from the combination of aminosilane precursors and chlorosilane precursor. The '792 application describes aminosilane precursors comprising an aminochlorosilane having the formula $Cl_{4-x}Si(NR'R")_x$ wherein x=2 or 3, R' and R" are independently selected from H or an alkyl group, and R' and R" may be linked to form a ring structure and the aminoalkylsilane precursors having the formula $R'''_{4-x}Si(NR'R")_x$ wherein x=1,2, or 3, R' and R" are independently selected from H or an alkyl group, R' and R" may be linked to form a ring structure and R''' is an alkyl group having less than 3 carbons.

The reference "Substitution of chlorine in silicon tetrachloride by dimethyl, diethylamino, and piperidino groups", Breederveld, et al., Research (London) 5:537-9 (1952) describes synthesizing dialkylaminochlorosilanes by the stepwise replace of atoms in $SiCl_4$ with dialkylamino groups to produce one or more of the following compounds: diethylaminotrichlorosilane, di(diethylamino)dichlorosilane, tri(diethylamino)chlorosilane or tetra(diethylamino)silane. A similar procedure was used to prepare piperidinotrichlorosilane and dipiperidinodichlorosilane.

The reference "Molecular structures of some (dimethylamino)halogenosilanes in the gas phase by electron diffraction and the crystal and molecular structures on mono- and di-chloro(dimethylamino)silane by x-ray diffraction at low temperatures", Anderson et al., J. Chem. Soc., (1987) describes (dimethylamino)halogensilanes $SiH_2X(NMe_2)$ wherein X=Cl, Br. Or I.

The reference "Chloroaminosilanes. I. Preparation of chloro(dimethylamino)hydrogen silanes", Washburne et al., Inorg. Nucl. Chem., 5(1):17-19 (1969) describes the preparation of $HSiCl_2NMe_2$ (I), $HSiCl(NMe_2)_2$ (II), and $HSi(NMe_2)_3$ (III) and the related chemical properties of these compounds.

The reference "Preparation of β-cyanoethyltrichlorosilane using silylamine catalysts", Pike et al., Journal of Organic Chemistry, 27(6): 21-90-92 (1962), describes silylamines of the type $(CH_3)_3SiNR_2$ which are shown to be directive catalysts by the addition of trichlorosilane to acrylonitrile. An example of a silylamine described in the reference is $(^iPr_2N)SiCl_2H$.

There is a need in the art to provide precursors that can be used to deposit films comprising silicon that provide one or more of the following advantages: low processing temperatures (e.g., 300° C. or below); relatively good deposition rate; compositional uniformity; and/or high purity.

BRIEF SUMMARY OF THE INVENTION

Described herein are halogenated organoaminosilane precursors and methods using same for forming films comprising silicon, such as, but not limited to, silicon films, silicon oxide, carbon doped silicon oxide, silicon nitride, silicon oxynitride, silicon carbide, silicon carbonitride, and combinations thereof onto at least a portion of a substrate. Also disclosed herein are the methods to form dielectric films or coatings on an object to be processed, such as, for example, a semiconductor wafer. In one embodiment of the method described herein, a layer comprising silicon and oxygen is deposited onto a substrate using a halogenated organoaminosilane precursor, optionally one or more additional non-halogenated organoaminosilane precursors, and an oxidizing agent in a deposition chamber under conditions for generating a silicon oxide layer on the substrate. In another embodiment of the method described herein, a layer comprising silicon and nitrogen is deposited onto a substrate using a halogenated precursor, optionally one or more non-halogenated organoaminosilane precursors, and a nitrogen containing precursor in a deposition chamber under conditions for generating a silicon nitride layer on the substrate. In a further embodiment, the halogenated organoaminosilane precursors described herein can also be used as a dopant for metal containing films, such as but not limited to, metal oxide films or metal nitride films. In the processes described herein, halogenated organoaminosilane having Formula I described herein is employed as at least one of the silicon containing precursors.

In one aspect, the halogenated organoaminosilane precursor described herein comprises an a silicon precursor having the following Formula I:

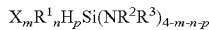
$$X_mR^1{}_nH_pSi(NR^2R^3)_{4-m-n-p} \qquad I$$

wherein X is a halide selected from the group consisting of Cl, Br, I; $R^1$ is independently selected from a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl, and a $C_6$ to $C_{10}$ aryl group; $R^2$ is selected from a linear or branched $C_1$ to $C_{10}$ alkyl, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; m is 1 or 2; n is 0, 1, or 2; p is 0, 1 or 2; and the sum of (m+n+p) is less than 4 and wherein $R^2$ and $R^3$ are linked to form a ring or $R^2$ and $R^3$ are not linked to form a ring. In certain embodiments, $R^2$ and $R^3$ in Formula I can be linked together to form a ring. In the other embodiments, $R^2$ and $R^3$ in Formula I are not linked together to form a ring.

In another aspect, there is provided a method for forming a silicon-containing film on at least one surface of a substrate comprising:

providing the at least one surface of the substrate in a reaction chamber; and forming the silicon-containing film on the at least one surface by a deposition process chosen from a chemical vapor deposition process and an atomic layer deposition process using a halogenated organoaminosilane precursor having the following Formula I:

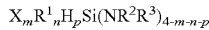
$$X_mR^1{}_nH_pSi(NR^2R^3)_{4-m-n-p} \qquad I$$

wherein X is a halide selected from the group consisting of Cl, Br, I; $R^1$ is independently selected from a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl, and a $C_6$ to $C_{10}$ aryl group; $R^2$ is selected from a linear or branched $C_1$ to $C_{10}$ alkyl, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; m is 1 or 2; n is 0, 1, or 2; p is 0, 1 or 2; and the sum of (m+n+p) is less than 4 and wherein $R^2$ and $R^3$ are linked to form a ring or $R^2$ and $R^3$ are not linked to form a ring. In one particular embodiment of Formula I, $R^2$ and $R^3$ can be linked together to form a ring. In another embodiment of Formula I, $R^2$ and $R^3$ are not linked together to form a ring.

In another aspect, there is provided a method of forming a silicon oxide film via an atomic layer deposition process or cyclic chemical vapor deposition process, the method comprising the steps of:

a. providing a substrate in a reactor;
b. introducing into the reactor an at least one silicon precursor selected from an at least one halogenated organoaminosilane precursor represented by the following Formula I:

$$X_mR^1{}_nH_pSi(NR^2R^3)_{4-m-n-p} \qquad I$$

wherein X is a halide selected from the group consisting of Cl, Br, I; $R^1$ is independently selected from a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl, and a $C_6$ to $C_{10}$ aryl group; $R^2$ is selected from a linear or branched $C_1$ to $C_{10}$ alkyl, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; m is 1 or 2; n is 0, 1, or 2; p is 0, 1 or 2; and the sum of (m+n+p) is less than 4 and wherein $R^2$ and $R^3$ are linked to form a ring or $R^2$ and $R^3$ are not linked to form a ring;

c. purging the reactor with a purge gas;
d. introducing an oxygen source into the reactor;
e. purging the reactor with a purge gas; and
repeating the steps b through e until a desired thickness of the film is obtained.

In a further aspect, there is provided a method of forming a silicon oxide film onto at least a surface of a substrate using a CVD process comprising:

a. providing a substrate in a reactor;
b. introducing into the reactor an at least one halogenated organoaminosilane precursor represented by the following Formula I:

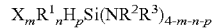
$$X_mR^1{}_nH_pSi(NR^2R^3)_{4-m-n-p} \qquad I$$

wherein X is a halide selected from the group consisting of Cl, Br, I; $R^1$ is independently selected from a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl, and a $C_6$ to $C_{10}$ aryl group; $R^2$ is selected from a linear or branched $C_1$ to $C_{10}$ alkyl, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; m is 1 or 2; n is 0, 1, or 2; p is 0, 1 or 2; and the sum of (m+n+p) is less than 4 and wherein $R^2$ and $R^3$ are linked to form a ring or $R^2$ and $R^3$ are not linked to form a ring; and c. providing an oxygen source to deposit the silicon oxide film onto the at least one surface.

In another aspect, there is provided a method of forming a silicon nitride film via an atomic layer deposition process or cyclic chemical vapor deposition process, the method comprising the steps of:

a. providing a substrate in a reactor;
b. introducing into the reactor an at least one silicon precursor represented by the following Formula I:

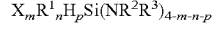
$$X_mR^1{}_nH_pSi(NR^2R^3)_{4-m-n-p} \qquad I$$

wherein X is a halide selected from the group consisting of Cl, Br, I; $R^1$ is independently selected from a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl, and a $C_6$ to $C_{10}$ aryl group; $R^2$ is selected from a linear or branched $C_1$ to $C_{10}$ alkyl, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; m is 1 or 2; n is 0, 1, or 2; p is 0, 1 or 2; and the sum of (m+n+p) is less than 4 and wherein $R^2$ and $R^3$ are linked to form a ring or $R^2$ and $R^3$ are not linked to form a ring;

c. purging the reactor with a purge gas;
d. introducing a nitrogen-containing source into the reactor;
e. purging the reactor with a purge gas; and
repeating the steps b through e until a desired thickness of the silicon nitride film is obtained.

In a further aspect, there is provided a method of forming a silicon nitride film onto at least a surface of a substrate using a CVD process comprising:

a. providing a substrate in a reactor;
b. introducing into the reactor an at least one organoaminosilane precursor represented by the following Formula I:

     I wherein X is a halide selected from the group consisting of Cl, Br, I; $R^1$ is independently selected from a linear or branched $C_1$ to $C_{10}$ alkyl group, a C to $C_{12}$ alkenyl group, a $C_2$ to $C_{12}$ alkynyl group, a $C_4$ to $C_{10}$ cyclic alkyl, and a $C_6$ to $C_{10}$ aryl group; $R^2$ is selected from a linear or branched $C_1$ to $C_{10}$ alkyl, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; m is 1 or 2; n is 0, 1, or 2; p is 0, 1 or 2; and the sum of (m+n+p) is less than 4 and wherein $R^2$ and $R^3$ are linked to form a ring or $R^2$ and $R^3$ are not linked to form a ring; and c. providing a nitrogen-containing source wherein the at least one organoaminosilane precursors and the nitrogen-containing source react to deposit the film comprising both silicon and nitrogen onto the at least one surface.

In another aspect, a vessel for depositing a dielectric film comprising one or more halogenated organoaminosilane precursor having Formula I is described herein. In one particular embodiment, the vessel comprises at least one pressurizable vessel (preferably of stainless steel) fitted with the proper valves and fittings to allow the delivery of one or more precursors to the reactor for a CVD or an ALD process.

In yet another aspect, there is provided a composition for the deposition of a dielectric film comprising:

     I wherein X is a halide selected from the group consisting of Cl, Br, I; $R^1$ is independently selected from a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl, and a $C_6$ to $C_{10}$ aryl group; $R^2$ is selected from a linear or branched $C_1$ to $C_{10}$ alkyl, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; m is 1 or 2; n is 0, 1, or 2; p is 0, 1 or 2; and the sum of (m+n+p) is less than 4 and wherein $R^2$ and $R^3$ are linked to form a ring or $R^2$ and $R^3$ are not linked to form a ring; and a solvent selected from the group consisting of an ether, a tertiary amine, a nitrile, an alkyl hydrocarbon, an aromatic hydrocarbon, a tertiary amino ether, or mixtures thereof.

BRIEF DESCRIPTION OF SEVERAL VIEWS OF THE DRAWINGS

FIG. 1 provides the mass spectroscopy (MS) spectrum of 2,6-dimethylpiperidinodichlorosilane described in Example 3.

DETAILED DESCRIPTION OF THE INVENTION

Halogenated organoaminosilanes are used as precursors to form stoichiometric and non-stoichiometric silicon containing films such as, but not limited to, silicon, amorphous silicon, crystalline silicon, microcrystalline silicon, polycrystalline, silicon oxide, carbon doped silicon oxide, silicon nitride, silicon oxynitride and silicon oxycarbonitride. These precursors can also be used, for example, as dopants for metal containing films. The halogenated organoaminosilane precursors are typically high purity volatile liquid precursor chemical that are vaporized and delivered to a deposition chamber or reactor as a gas to deposit a silicon containing film via CVD or ALD processes for semiconductor devices. In other embodiments, the halogenated organoaminosilanes can be used in a liquid-based deposition or film formation method such as, but not limited to, spin-on, dip coat, aerosol, ink jet, screen printing or spray application. The selection of precursor materials for deposition depends upon the desired resultant dielectric material or film. For example, a precursor material may be chosen for its content of chemical elements, its stoichiometric ratios of the chemical elements, and/or the resultant dielectric film or coating that are formed under CVD. The precursor material may also be chosen for various other characteristics such as cost, non-toxicity, handling characteristics, ability to maintain liquid phase at room temperature, volatility, molecular weight, and/or other considerations. In certain embodiments, the precursors described herein can be delivered to the reactor system by any number of means, preferably using a pressurizable stainless steel vessel fitted with the proper valves and fittings, to allow the delivery of liquid phase precursor to the deposition chamber or reactor.

It is believed that the halogenated organoaminosilanes precursors described herein may provide better reactivity towards substrate surface during chemical vapor deposition, particularly cyclic CVD deposition, or atomic layer deposition to form Si—N—Si linkage, Si—Si bonds, Si—O—Si linkage via in situ catalytic reaction to release organoamine and HCl, which then combine to form amine-hydrogen chloride salt, compared to non-halogenated organoaminosilanes. It is believed that one particular advantage of the halogenated organoaminosilane precursors compared to conventional silicon precursors such as silicon tetrachloride or organoaminosilanes is that both the halide and the organoamino groups can react with Si—OH or $SiNH_2$ on the substrate surface to anchor the precursors during ALD or CCVD process, thus facilitating the deposition of silicon-containing films. In addition to the foregoing advantages, in certain embodiments such as for depositing a silicon oxide or silicon nitride film using a cyclic CVD, an ALD, or PEALD deposition method, the halogenated organoaminosilane precursor described herein may be able to deposit high density materials at relatively low deposition temperatures, e.g., at 500° C. or less, at 400° C. or less, or at 300° C. or less. In other embodiments, the precursors described herein can be used, for example, in higher temperature deposition at temperatures ranging from about 500° C. to about 800° C.

In one aspect, there is provided certain precursors or halogenated organoaminosilanes that are represented by the following Formula I:

     I wherein X is a halide selected from the group consisting of Cl, Br, I; $R^1$ is independently selected from a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl, and a $C_6$ to $C_{10}$ aryl group; $R^2$ is selected from a linear or branched $C_1$ to $C_{10}$ alkyl, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; m is 1 or 2; n is 0, 1, or 2; p is 0, 1 or 2; and the sum of (m+n+p) is less than 4 and wherein R² and R³ are linked to form a ring or R² and R³ are not linked to form a ring. In certain embodiments of the halogenated organoaminosilane of Formula I, R² and R³ can be linked together to form a ring. In alternative embodiments of the halogenated organoaminosilane of Formula I, R² and R³ are not linked together to form a ring.

In Formulas I-III and throughout the description, the term "alkyl" denotes a linear, or branched functional group having from 1 to 10 or 1 to 4 carbon atoms. Exemplary alkyl groups include, but are not limited to, methyl, ethyl, n-propyl, iso-propyl, n-butyl, isobutyl, sec-butyl, tert-butyl, n-pentyl, iso-pentyl, tert-pentyl, hexyl, isohexyl, and neohexyl. In certain embodiments, the alkyl group may have one or more functional groups such as, but not limited to, an alkoxy group, a dialkylamino group or combinations thereof, attached thereto. In other embodiments, the alkyl group does not have one or more functional groups attached thereto.

In Formulas I-III and throughout the description, the term "cyclic alkyl" denotes a cyclic functional group having from 3 to 12 or from 4 to 10 carbon atoms. Exemplary cyclic alkyl groups include, but are not limited to, cyclobutyl, cyclopentyl, cyclohexyl, and cyclooctyl groups.

In Formulas I-III and throughout the description, the term "aryl" denotes an aromatic cyclic functional group having from 6 to 12 carbon atoms. Exemplary aryl groups include, but are not limited to, phenyl, benzyl, chlorobenzyl, tolyl, and o-xylyl.

In Formulas I-III and throughout the description, the term "alkenyl group" denotes a group which has one or more carbon-carbon double bonds and has from 2 to 12 or from 2 to 6 carbon atoms. Exemplary alkenyl groups include, but are not limited to, vinyl or allyl groups In Formulas I-III and throughout the description, the term "alkynyl group" denotes a group which has one or more carbon-carbon triple bonds and has from 2 to 12 or from 2 to 6 carbon atoms.

In Formulas I-III and throughout the description, the term "alkoxy" denotes an alkyl group which has is linked to an oxygen atom (e.g., R—O) and may have from 1 to 12, or from 1 to 6 carbon atoms. Exemplary alkoxy groups include, but are not limited to, methoxy (—OCH₃), ethoxy(—OCH₂CH₃), n-propoxy (—OCH₂CH₂CH₃), and iso-propoxy (—OCHMe₂).

In certain embodiments, one or more of the alkyl group, alkenyl group, alkynyl group, alkoxy group, and/or aryl group in Formulas I-III may be substituted or have one or more atoms or group of atoms substituted in place of, for example, a hydrogen atom. Exemplary substituents include, but are not limited to, oxygen, sulfur, halogen atoms (e.g., F, Cl, I, or Br), nitrogen, and phosphorous. In other embodiments, one or more of the alkyl group, alkenyl group, alkynyl group, alkoxy group, and/or aryl in Formula I may be unsubstituted.

In certain embodiments, substituents R² and R³ are linked in Formula I to form a ring structure. In other embodiments, substituent R² and R³ are not linked in Formula I.

The following Table 1 provides some non-limiting examples of certain embodiments of the organoaminosilanes having Formula I.

TABLE 1

Exemplary Organoaminosilanes Having Formula I

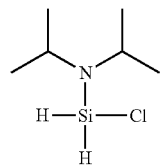

Di-iso-propylaminochlorosilane

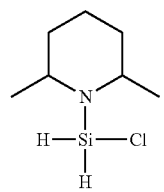

2,6-dimethylpiperidinochlorosilane

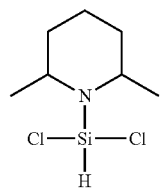

2,6-dimethyl-piperidinodichlorosilane

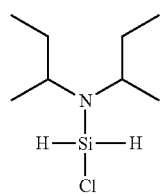

Di-sec-buylaminochlorosilane

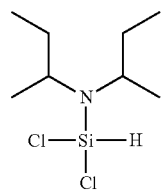

Di-sec-buylaminodichlorosilane

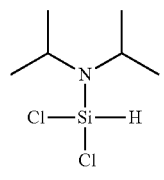

Di-iso-propylaminodichlorosilane

TABLE 1-continued

Exemplary Organoaminosilanes Having Formula I

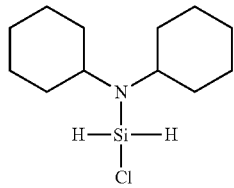

Dicyclohexylaminochlorosilane

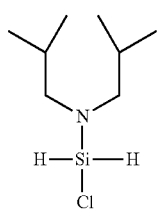

Di-iso-butylaminochlorosilane

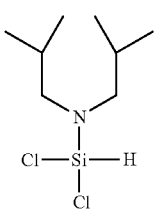

Di-iso-butylaminodichlorosilane

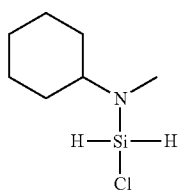

Cyclohexylmethylaminochlorosilane

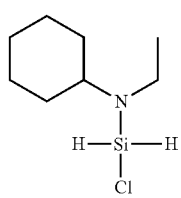

Cyclohexylethylaminochlorosilane

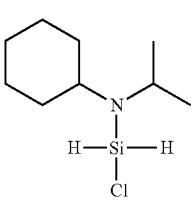

Cyclohexyl-iso-propylaminochlorosilane

TABLE 1-continued

Exemplary Organoaminosilanes Having Formula I

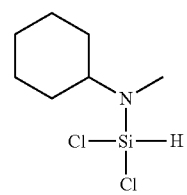

Cyclohexylmethylaminodichlorosilane

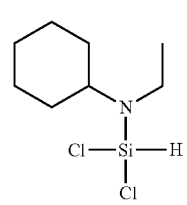

Cyclohexylethylaminodichlorosilane

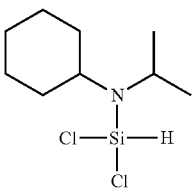

Cyclohexyl-iso-propylaminodichlorosilane

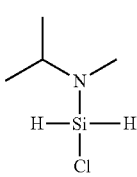

Iso-propylmethylaminochlorosilane

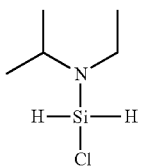

Iso-propylethylaminochlorosilane

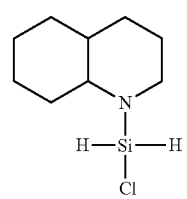

N-(chlorosilyl)perhydroquinoline

TABLE 1-continued

Exemplary Organoaminosilanes Having Formula I

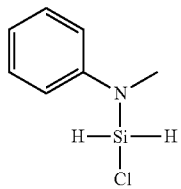

Phenylmethylaminochlorosilane

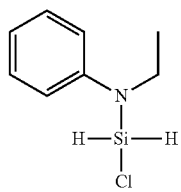

Phenylethylaminochlorosilane

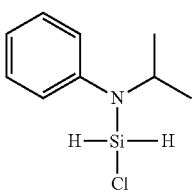

Phenyl-iso-propylaminoclorosilane

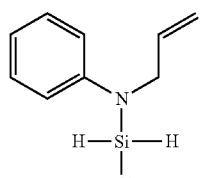

Phenylallylaminochlorosilane

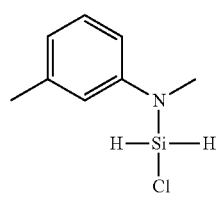

m-tolylmethylaminochlorosilane

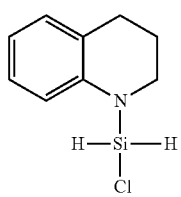

N-(chlorosilyl)-tetrahydroquinoline

TABLE 1-continued

Exemplary Organoaminosilanes Having Formula I

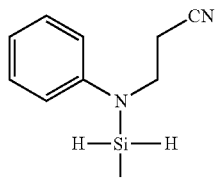

N-chlorosilyl-3-anilinopropionitrile

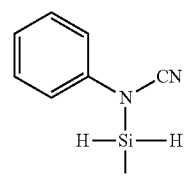

N-chlorosilyl-N-phenylglycinonitrile

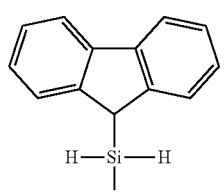

N-(chlorosilyl)carbazole

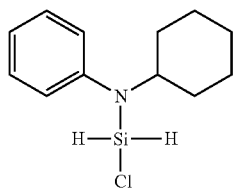

Phenylcyclohexylaminochlorosilane

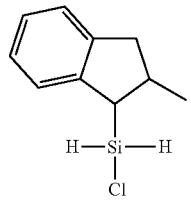

N-(chlorosilyl)-2-methylindoline

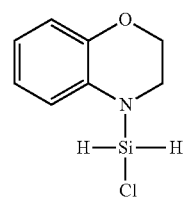

N-(chlorosilyl)benzomorpholine

TABLE 1-continued

Exemplary Organoaminosilanes Having Formula I

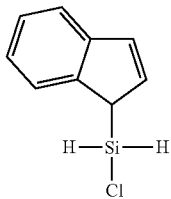
N-(chlorosilyl)indole

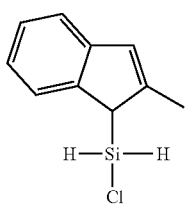
N-(chlorosilyl)-2-methylindole

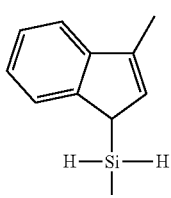
N-(chlorosilyl)-3-methylindoline

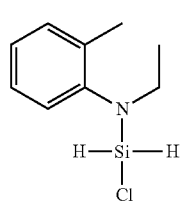
o-tolylethylaminochlorosilane

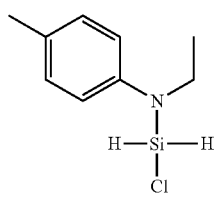
p-tolylethylaminochlirosilane

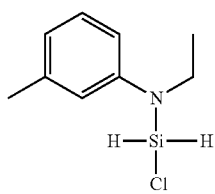
m-tolylethylaminochlorosilane

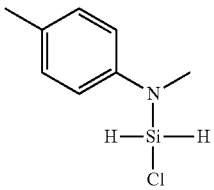
p-tolylmethylaminochlorosilane

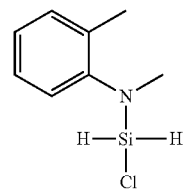
o-tolylmethylaminochlorosilane

N-(chlorosilyl)-1,2,3,4-tetrahydro-2-methylquinoline

In certain embodiments, the halogenated organoaminosilane of Formula I comprises Cl as X and is selected from the group comprising: $ClH_2Si(NR^2R^3)$ wherein m=1, n=0, p=2, $R^2$ is selected from a linear or branched $C_3$ to $C_{10}$ alkyl group and a $C_6$ to $C_{10}$ aryl group and $R^3$ is a branched $C_3$ to $C_{10}$ alkyl group or a $C_6$ to $C_{10}$ aryl group and wherein $R^2$ and $R^3$ can form a cyclic or alkyl substituted cyclic ring; and $R^1ClHSi(NR^3R^4)$ wherein m=1, n=1, p=1, $R^1$ is a $C_1$ to $C_{10}$ alkyl group and $R^2$ and $R^3$ are a linear or branched $C_3$ to $C_{10}$ alkyl group or a $C_4$ to $C_{10}$ aryl group and wherein $R^2$ and $R^3$ can form a cyclic or a alkyl substituted cyclic ring.

In certain embodiments, the halogenated organoaminosilanes having Formula I can be prepared by reacting 1 molar equivalent dichlorosilane (DCS) with 1 molar equivalent secondary amine or trichlorosilane (TCS) with 1 or 2 molar equivalent secondary amine having the following Formula II in an organic solvent or solvent mixture, using 1 or 2 molar equivalent tertiary amine such as triethylamine or tributylamine to absorb the byproduct, hydrogen chloride, preferably a tertiary amine is employed as demonstrated in Example 1 and 2 below). In certain embodiments, tertiary amines are replaced by equal molar of secondary amines. Selected secondary amines that can be used in this embodiment have following Formula II:

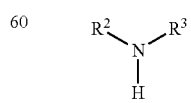

II $R^2$ is selected from a linear or branched $C_1$ to $C_{10}$ alkyl, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group and wherein $R^2$ and $R^3$ are linked to form a ring or $R^2$ and $R^3$ are not linked to form a ring. In embodiments where $R^2$ and/or $R^3$ are branched alkyl, cyclic alkyl, or aromatic groups, the stability of the halogenated organoaminosilanes synthesized from these amines may be greatly improved, since the intermolecular substitute exchange reaction of amino groups and halogen atoms are hindered be the steric bulkiness of such $R^2$ and/or $R^3$ groups. Exemplary secondary amines having Formula II include, but are not limited to, di-iso-propylamine, di-iso-butylamine, di-sec-butylamine, iso-propylmethylamine, iso-propylethylamine, cyclohexylmethylamine, cyploroylethylamine, dicyclopropylamine, cyclohexylisopropylamine, N-methylaniline(phenylmethylamine), N-ethylaniline (phenylethylamine), N-iso-propylaniline, n-Butylaniline, N-allylaniline, N-Ethyl-m-toluidine, N-Methyl-o-toluidine, N-Methyl-p-toluidine, 4-fluoro-N-methylaniline, 4-Chloro-N-methylaniline, N-cyclohexylaniline, 3-anilinopropionitrile, or N-phenylglycinonitrile.

Exemplary amines having Formula II wherein $R^2$ and $R^3$ are linked to form a ring include, but are not limited to, 2,6-dimethylpiperidine, 2-methylpiperidine, 2-methylpyrrolidine, 2,5-dimethylpyrrolidine, 2,2,6,6,-tetramethylpiperidine, 3-methylindole, 2-methylindole, indole, perhydroquinoline, 8-methyl-1,2,3,4-tetrahydroquinoline, 3-indoleacetonitrile, 2-methylindoline, 2,3-dihydroindole, 5-methylindoline, 1,2,3,4-tetrahydroquinoline, 1,2,3,4-tetrahydro-2-methylquinoline, 1,2,3,4-tetrahydro-6-methylquinoline, 3,4-dihydro-2H-1,4-benzoxazine, carbazole, 2,6-dim ethylmorpholine and 3,5-dimethylmorpholine.

The following Equations 1, 2 and 3 provide examples of reaction schemes or synthesis routes which may be used to make the halogenated organoaminosilanes having Formula I as described herein. The reactions in Equations 1, 2, and 3 can be conducted with (e.g., in the presence of) organic solvents. In embodiments wherein an organic solvent is used, examples of suitable organic solvents include, but are not limited to, hydrocarbon such as hexanes, octane, toluene, and ethers such as diethylether, and tetrahydrofuran (THF). In these or other embodiments, the reaction temperature is in the range of from about −70° C. to the boiling point of the solvent employed if a solvent is involved. The resulting organoaminosilane can be purified via vacuum distillation after removing all by-products as well as solvent(s). Equation 1-3 are embodiments involving reaction of dichlorosilane or trichlorosilane. Examples of the synthetic route involving partial amination reaction are provided herein as Example 1 and 3 whereas Equation 2 involving metal amide which can be prepared via reaction of an amine with Formula II with metal alkyl is demonstrated in Example 2.

Equation 1

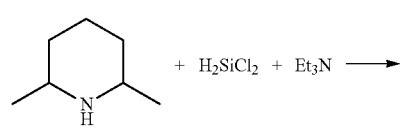

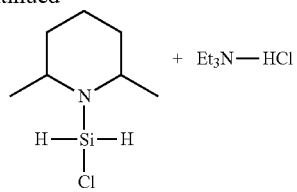

Equation 2

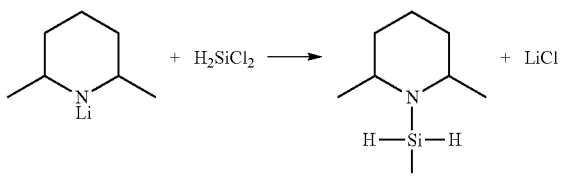

Equation 3

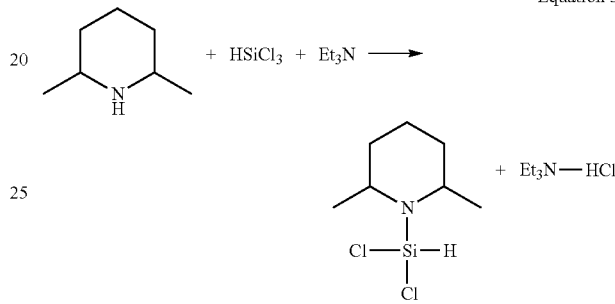

The method used to form the silicon-containing dielectric films or coatings are deposition processes. Examples of suitable deposition processes for the method disclosed herein include, but are not limited to, cyclic CVD (CCVD), MOCVD (Metal Organic CVD), thermal chemical vapor deposition, plasma enhanced chemical vapor deposition ("PECVD"), high density PECVD, photon assisted CVD, plasma-photon assisted ("PPECVD"), cryogenic chemical vapor deposition, chemical assisted vapor deposition, hot-filament chemical vapor deposition, CVD of a liquid polymer precursor, deposition from supercritical fluids, and low energy CVD (LECVD). In certain embodiments, the metal containing films are deposited via atomic layer deposition (ALD), plasma enhanced ALD (PEALD) or plasma enhanced cyclic CVD (PECCVD) process. As used herein, the term "chemical vapor deposition processes" refers to any process wherein a substrate is exposed to one or more volatile precursors, which react and/or decompose on the substrate surface to produce the desired deposition. As used herein, the term "atomic layer deposition process" refers to a self-limiting (e.g., the amount of film material deposited in each reaction cycle is constant), sequential surface chemistry that deposits films of materials onto substrates of varying compositions. Although the precursors, reagents and sources used herein may be sometimes described as "gaseous", it is understood that the precursors can be either liquid or solid which are transported with or without an inert gas into the reactor via direct vaporization, bubbling or sublimation. In some case, the vaporized precursors can pass through a plasma generator. In one embodiment, the dielectric film is deposited using an ALD process. In another embodiment, the dielectric film is deposited using a CCVD process. In a further embodiment, the dielectric film is deposited using a thermal CVD process. The term "reactor" as used herein, includes without limitation, reaction chamber or deposition chamber.

In certain embodiments, the method disclosed herein avoids pre-reaction of the precursors by using ALD or CCVD methods that separate the precursors prior to and/or during the introduction to the reactor. In this connection, deposition techniques such as ALD or CCVD processes are used to deposit the dielectric film. In one embodiment, the film is deposited via an ALD process by exposing the substrate surface alternatively to the one or more the silicon-containing precursor, oxygen source, nitrogen-containing source, or other precursor or reagent. Film growth proceeds by self-limiting control of surface reaction, the pulse length of each precursor or reagent, and the deposition temperature. However, once the surface of the substrate is saturated, the film growth ceases.

In certain embodiments, the method described herein further comprises one or more additional silicon-containing precursors or non-halogenated other than the halogenated organoaminosilane precursor having the above Formula I. Examples of additional silicon-containing precursors include, but are not limited to, organo-silicon compounds such as siloxanes (e.g., hexamethyl disiloxane (HMDSO) and dimethyl siloxane (DMSO)); organosilanes (e.g., methylsilane; dimethylsilane; vinyl trimethylsilane; trimethylsilane; tetramethylsilane; ethylsilane; disilylmethane; 2,4-disilapentane; 1,4-disilabutane; 2,5-disilahexane; 2,2-disilylpropane; 1,3,5-trisilacyclohexane, and fluorinated derivatives of these compounds; phenyl-containing organo-silicon compounds (e.g., dimethylphenylsilane and diphenylmethylsilane); oxygen-containing organo-silicon compounds,e.g., dimethyldimethoxysilane; 1,3,5,7-tetramethylcyclotetrasiloxane; 1,1,3,3-tetramethyldisiloxane; 1,3,5,7-tetrasila-4-oxo-heptane; 2,4,6,8-tetrasila-3,7-dioxo-nonane; 2,2-dimethyl-2,4,6,8-tetrasila-3,7-dioxo-nonane; octamethylcyclotetrasiloxane; [1,3,5,7,9]-pentamethylcyclopentasiloxane; 1,3,5,7-tetrasila-2,6-dioxo-cyclooctane; hexamethylcyclotrisiloxane; 1,3-dimethyldisiloxane; 1,3,5,7,9-pentamethylcyclopentasiloxane; hexamethoxydisiloxane, and fluorinated derivatives of these compounds.

In one particular embodiment of the method described herein, the non-halogenated, silicon-containing precursor is a compound having the following Formula III:

(R²R³N)SiH₃ (III)

wherein $R^2$ is selected from a linear or branched $C_1$ to $C_{10}$ alkyl, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group and wherein $R^2$ and $R^3$ are linked to form a ring or $R^2$ and $R^3$ are not linked to form a ring. In certain embodiments of Formula III, $R^2$ and $R^3$ can be combined to form a cyclic group or ring. In other embodiments of Formula III $R^2$ and $R^3$ are not combined to form a cyclic group or ring. Examples of non-halogenated silicon-containing precursors include, but are not limited to, di-isopropylaminosilane, di-sec-butylaminosilane, phenylmethylaminosilane, and 2,6-dimethylpiperidinosilane.

Depending upon the deposition method, in certain embodiments, the one or more, halogenated or non-halogenated, silicon-containing precursors may be introduced into the reactor at a predetermined molar volume, or from about 0.1 to about 1000 micromoles. In this or other embodiments, the halogenated or non-halogenated organoaminosilane precursor may be introduced into the reactor for a predetermined time period. In certain embodiments, the time period ranges from about 0.001 to about 500 seconds.

In certain embodiments, the dielectric films deposited using the methods described herein are formed in the presence of oxygen using an oxygen source, reagent or precursor comprising oxygen. An oxygen source may be introduced into the reactor in the form of at least one oxygen source and/or may be present incidentally in the other precursors used in the deposition process. Suitable oxygen source gases may include, for example, water ($H_2O$) (e.g., deionized water, purifier water, and/or distilled water), oxygen ($O_2$), oxygen plasma, ozone ($O_3$), NO, $NO_2$, carbon monoxide (CO), carbon dioxide ($CO_2$) and combinations thereof. In certain embodiments, the oxygen source comprises an oxygen source gas that is introduced into the reactor at a flow rate ranging from about 1 to about 2000 square cubic centimeters (sccm) or from about 1 to about 1000 sccm. The oxygen source can be introduced for a time that ranges from about 0.1 to about 100 seconds. In one particular embodiment, the oxygen source comprises water having a temperature of 10° C. or greater. In embodiments wherein the film is deposited by an ALD or a cyclic CVD process, the precursor pulse can have a pulse duration that is greater than 0.01 seconds, and the oxygen source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between. The oxygen source or reagent is provided in a molecular amount less than a 1:1 ratio to the silicon precursor, so that at least some carbon is retained in the as deposited dielectric film.

In certain embodiments, the dielectric films comprise silicon and nitrogen. In these embodiments, the dielectric films deposited using the methods described herein are formed in the presence of nitrogen-containing source. An nitrogen-containing source may be introduced into the reactor in the form of at least one nitrogen source and/or may be present incidentally in the other precursors used in the deposition process. Suitable nitrogen-containing source gases may include, for example, ammonia, hydrazine, monoalkylhydrazine, dialkylhydrazine, nitrogen, nitrogen/hydrogen, ammonia plasma, nitrogen plasma, nitrogen/hydrogen plasma, and mixture thereof. In certain embodiments, the nitrogen-containing source comprises an ammonia plasma or hydrogen/nitrogen plasma source gas that is introduced into the reactor at a flow rate ranging from about 1 to about 2000 square cubic centimeters (sccm) or from about 1 to about 1000 sccm. The nitrogen-containing source can be introduced for a time that ranges from about 0.1 to about 100 seconds. In embodiments wherein the film is deposited by an ALD or a cyclic CVD process, the precursor pulse can have a pulse duration that is greater than 0.01 seconds, and the nitrogen-containing source can have a pulse duration that is less than 0.01 seconds, while the water pulse duration can have a pulse duration that is less than 0.01 seconds. In yet another embodiment, the purge duration between the pulses that can be as low as 0 seconds or is continuously pulsed without a purge in-between.

The deposition methods disclosed herein may involve one or more purge gases. The purge gas, which is used to purge away unconsumed reactants and/or reaction byproducts, is an inert gas that does not react with the precursors. Exemplary purge gases include, but are not limited to, argon (Ar), nitrogen ($N_2$), helium (He), neon, hydrogen ($H_2$), and mixtures thereof. In certain embodiments, a purge gas such as Ar is supplied into the reactor at a flow rate ranging from about 10 to about 2000 sccm for about 0.1 to 1000 seconds, thereby purging the unreacted material and any byproduct that may remain in the reactor.

The respective step of supplying the precursors, oxygen source, the nitrogen-containing source, and/or other precursors, source gases, and/or reagents may be performed by changing the time for supplying them to change the stoichiometric composition of the resulting dielectric film.

Energy is applied to the at least one of the precursor, nitrogen-containing source, reducing agent, other precursors or combination thereof to induce reaction and to form the dielectric film or coating on the substrate. Such energy can be provided by, but not limited to, thermal, plasma, pulsed plasma, helicon plasma, high density plasma, inductively coupled plasma, X-ray, e-beam, photon, remote plasma methods, and combinations thereof. In certain embodiments, a secondary RF frequency source can be used to modify the plasma characteristics at the substrate surface. In embodiments wherein the deposition involves plasma, the plasma-generated process may comprise a direct plasma-generated process in which plasma is directly generated in the reactor, or alternatively a remote plasma-generated process in which plasma is generated outside of the reactor and supplied into the reactor.

The organoaminosilane precursors and/or other silicon-containing precursors may be delivered to the reaction chamber such as a CVD or ALD reactor in a variety of ways. In one embodiment, a liquid delivery system may be utilized. In an alternative embodiment, a combined liquid delivery and flash vaporization process unit may be employed, such as, for example, the turbo vaporizer manufactured by MSP Corporation of Shoreview, Minn., to enable low volatility materials to be volumetrically delivered, which leads to reproducible transport and deposition without thermal decomposition of the precursor. In liquid delivery formulations, the precursors described herein may be delivered in neat liquid form, or alternatively, may be employed in solvent formulations or compositions comprising same. Thus, in certain embodiments the precursor formulations may include solvent component(s) of suitable character as may be desirable and advantageous in a given end use application to form a film on a substrate.

For those embodiments wherein the halogenated organoaminosilane precursor(s) having Formula I is used in a composition comprising a solvent and an halogenated organoaminosilane precursor having Formula I described herein, the solvent or mixture thereof selected does not react with the organoaminosilane. The amount of solvent by weight percentage in the composition ranges from 0.5% by weight to 99.5% or from 10% by weight to 75%. In this or other embodiments, the solvent has a boiling point (b.p.) similar to the b.p. of the halogenated organoaminosilane of Formula I or the difference between the b.p. of the solvent and the b.p. of the halogenated organoaminosilane of Formula I is 40° C. or less, 30° C. or less, or 20° C. or less, or 10° C. Alternatively, the difference between the boiling points ranges from any one or more of the following end-points: 0, 10, 20, 30, or 40° C. Examples of suitable ranges of b.p. difference include without limitation, 0 to 40° C., 20° to 30° C., or 10° to 30° C. Examples of suitable solvents in the compositions include, but are not limited to, an ether (such as 1,4-dioxane, dibutyl ether), a tertiary amine (such as pyridine, 1-methylpiperidine, 1-ethylpiperidine, N,N'-Dimethylpiperazine, N,N,N',N'-Tetramethylethylenediamine), a nitrile (such as benzonitrile), an alkyl hydrocarbon (such as octane, nonane, dodecane, ethylcyclohexane), an aromatic hydrocarbon (such as toluene, mesitylene), a tertiary aminoether (such as bis(2-dimethylaminoethyl)ether), or mixtures thereof. Some non-limiting exemplary compositions include, but are not limited to, a composition comprising di-iso-propylaminosilane (b.p. about 116° C.) and octane (b.p. 125 to 126° C.); di-iso-propylaminosilane (b.p. about 116° C.) and pyridine (b.p. 115° C.); di-iso-propylaminosilane (b.p. about 116° C.) and toluene (b.p. 110° C.); a composition comprising N-methylcyclohexylaminosilane (b.p. about 171° C. and decane (b.p. 174° C.); a composition comprising N-methylcyclohexylaminosilane (b.p. about 171° C. and diethylene glycol dimethyl ether (b.p. 162° C.); a composition comprising N-iso-propylcyclohexylaminosilane (b.p. about 199° C.) and bis(2-dimethylaminoethyl)ether (b.p., 189° C.); N-iso-propylcyclohexylaminosilane (b.p. about 199° C.) and benzonitrile (b.p., 191° C.).

In another embodiment, a vessel for depositing a dielectric film comprising one or more organoaminosilane precursor having Formula I is described herein. In one particular embodiment, the vessel comprises at least one pressurizable vessel (preferably of stainless steel) fitted with the proper valves and fittings to allow the delivery of one or more precursors to the reactor for a CVD or an ALD process. In this or other embodiments, the halogenated organoaminosilane precursor of Formula I is provided in a pressurizable vessel comprised of stainless steel and the purity of the precursor is 98% by weight or greater or 99.5% or greater which is suitable for the majority of semiconductor applications. In certain embodiments, such vessels can also have means for mixing the precursors with one or more additional precursor if desired. In these or other embodiments, the contents of the vessel(s) can be premixed with an additional precursor. Alternatively, the halogenated organoaminosilane precursor and/or other precursor can be maintained in separate vessels or in a single vessel having separation means for maintaining the organoaminosilane precursor and other precursor separate during storage. In certain embodiments, the halogenated organoaminosilane precursor having Formula I in the vessel further comprises a back fill gas(es) such as, but not limited to, nitrogen, an inert gas such as helium, or combinations thereof. In an alternative embodiment, the vessel does not contain a back fill gas.

As previously mentioned, the purity level of the halogenated organoaminosilane is sufficiently high enough to be acceptable for reliable semiconductor manufacturing. In certain embodiments, the halogenated organoaminosilane precursors described herein comprise less than 2% by weight, or less than 1% by weight, or less than 0.5% by weight of one or more of the following impurities: free amines, free halides or an halogen ion, and higher molecular weight species. Higher purity levels of the organoaminosilanes described herein can be obtained through one or more of the following processes: purification, adsorption, and/or distillation.

In one embodiment of the method described herein, a cyclic deposition process such as CCVD, ALD, or PEALD may be employed, wherein at least one silicon-containing precursor selected from a halogenated organoaminosilane precursor having Formula I and optionally a nitrogen-containing source such as, for example, ammonia, hydrazine, monoalkylhydrazine, dialkylhydrazine, nitrogen, nitrogen/hydrogen, ammonia plasma, nitrogen plasma, nitrogen/hydrogen plasma are employed.

In certain embodiments, the gas lines connecting from the precursor canisters to the reaction chamber are heated to one or more temperatures depending upon the process requirements and the container of the halogenated organoaminosilane precursor having Formula I is kept at one or more temperatures for bubbling. In other embodiments, a solution comprising the at least one halogenated organoaminosilane precursor having Formula I is injected into a vaporizer kept at one or more temperatures for direct liquid injection.

A flow of argon and/or other gas may be employed as a carrier gas to help deliver the vapor of the at least one organoaminosilane precursor to the reaction chamber during the precursor pulsing. In certain embodiments, the reaction chamber process pressure is about 1 Torr.

In a typical ALD or CCVD process, the substrate such as a silicon oxide substrate is heated on a heater stage in a reaction chamber that is exposed to the silicon-containing precursor initially to allow the complex to chemically adsorb onto the surface of the substrate.

A purge gas such as argon purges away unabsorbed excess complex from the process chamber. After sufficient purging, a nitrogen-containing source may be introduced into reaction chamber to react with the absorbed surface followed by another gas purge to remove reaction by-products from the chamber. The process cycle can be repeated to achieve the desired film thickness.

In certain embodiments, the process employs a reducing agent. The reducing agent is typically introduced in gaseous form. Examples of suitable reducing agents include, but are not limited to, hydrogen gas, hydrogen plasma, remote hydrogen plasma, silanes (i.e., diethylsilane, ethylsilane, dimethylsilane, phenylsilane, silane, disilane, aminosilanes, chlorosilanes), boranes (i.e., borane, diborane), alanes, germanes, hydrazines, ammonia, or mixtures thereof. In one particular embodiment such as the deposition of amorphous silicon, a reducing agent is used.

In this or other embodiments, it is understood that the steps of the methods described herein may be performed in a variety of orders, may be performed sequentially or concurrently (e.g., during at least a portion of another step), and any combination thereof. The respective step of supplying the precursors and the nitrogen-containing source gases may be performed by varying the duration of the time for supplying them to change the stoichiometric composition of the resulting dielectric film.

In another embodiment of the method disclosed herein, the films containing both silicon and nitrogen are formed using a ALD deposition method that comprises the steps of:

providing a substrate in an ALD reactor;

introducing into the ALD reactor an at least one halogenated organoaminosilane precursor represented by the following Formula I:

$$X_m R^1_n H_p Si(NR^2 R^3)_{4-m-n-p} \qquad I$$

wherein X is a halide selected from the group consisting of Cl, Br, I; $R^1$ is independently selected from a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl, and a $C_6$ to $C_{10}$ aryl group; $R^2$ is selected from a linear or branched $C_1$ to $C_{10}$ alkyl, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; m is 1 or 2; n is 0, 1, or 2; p is 0, 1 or 2; and the sum of (m+n+p) is less than 4 and wherein $R^2$ and $R^3$ are linked to form a ring or $R^2$ and $R^3$ are not linked to form a ring;

chemisorbing the at least one halogenated organoaminosilane precursor onto a substrate;

purging away the unreacted at least one organoaminosilane precursor using a purge gas;

providing a nitrogen-containing source to the organoaminosilane precursor onto the heated substrate to react with the sorbed at least one organoaminosilane precursor; and optionally purging away any unreacted nitrogen-containing source.

In another embodiment of the method disclosed herein, the dielectric films is formed using a ALD deposition method that comprises the steps of:

providing a substrate in a reactor;

introducing into the reactor an at least one halogenated organoaminosilane precursor represented by the following Formula I:

$$X_m R^1_n H_p Si(NR^2 R^3)_{4-m-n-p} \qquad I$$

wherein X is a halide selected from the group consisting of Cl, Br, I; $R^1$ is independently selected from a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl, and a $C_6$ to $C_{10}$ aryl group; $R^2$ is selected from a linear or branched $C_1$ to $C_{10}$ alkyl, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; m is 1 or 2; n is 0, 1, or 2; p is 0, 1 or 2; and the sum of (m+n+p) is less than 4 and wherein $R^2$ and $R^3$ are linked to form a ring or $R^2$ and $R^3$ are not linked to form a ring;

chemisorbing the at least one organoaminosilane precursor onto a substrate;

purging away the unreacted at least one organoaminosilane precursor using a purge gas;

providing an oxygen source to the organoaminosilane precursor onto the heated substrate to react with the sorbed at least one organoaminosilane precursor; and optionally purging away any unreacted oxygen source.

The above steps define one cycle for the method described herein; and the cycle can be repeated until the desired thickness of a dielectric film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen source may be performed by varying the duration of the time for supplying them to change the stoichiometric composition of the resulting dielectric film, although always using oxygen in less than a stoichiometric amount relative to the available silicon.

For multi-component dielectric films, other precursors such as silicon-containing precursors, nitrogen-containing precursors, reducing agents, or other reagents can be alternately introduced into the reactor chamber.

In a further embodiment of the method described herein, the dielectric film is deposited using a thermal CVD process. In this embodiment, the method comprises:

placing one or more substrates into a reactor which is heated to a temperature ranging from ambient temperature to about 700° C. and maintained at a pressure of 1 Torr or less;

introducing at least one halogenated organoaminosilane precursor having the following Formula I:

$$X_m R^1_n H_p Si(NR^2 R^3)_{4-m-n-p} \qquad I$$

wherein X is a halide selected from the group consisting of Cl, Br, I; $R^1$ is independently selected from a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl, and a $C_6$ to $C_{10}$ aryl group; $R^2$ is selected from a linear or branched $C_1$ to $C_{10}$ alkyl, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; m is 1 or 2; n is 0, 1, or 2; p is 0, 1 or 2; and the sum of (m+n+p) is less than 4 and wherein $R^2$ and $R^3$ are linked to form a ring or $R^2$ and $R^3$ are not linked to form a ring; and providing an oxygen source into the reactor to at least partially react with the at least one organoaminosilane precursor and deposit a dielectric film onto the one or more substrates. In certain embodiments of the CVD method, the reactor is maintained at a pressure ranging from 100 mTorr to 600 mTorr during the introducing step.

The above steps define one cycle for the method described herein; and the cycle can be repeated until the desired thickness of a dielectric film is obtained. In this or other embodiments, it is understood that the steps of the methods described herein may be performed in a variety of orders, may be performed sequentially or concurrently (e.g., during at least a portion of another step), and any combination thereof. The respective step of supplying the precursors and oxygen source may be performed by varying the duration of the time for supplying them to change the stoichiometric composition of the resulting dielectric film, although always using oxygen in less than a stoichiometric amount relative to the available silicon.

For multi-component dielectric films, other precursors such as silicon-containing precursors, nitrogen-containing precursors, oxygen sources, reducing agents, and/or other reagents can be alternately introduced into the reactor chamber.

In a further embodiment of the method described herein, the dielectric film is deposited using a thermal CVD process. In this embodiment, the method comprises:

placing one or more substrates into a reactor which is heated to a temperature ranging from ambient temperature to about 700° C. and maintained at a pressure of 1 Torr or less;

introducing at least one halogenated organoaminosilane precursor having the following Formula I:

$$X_m R^1_n H_p Si(NR^2 R^3)_{4-m-n-p} \quad \text{I}$$

wherein X is a halide selected from the group consisting of Cl, Br, I; $R^1$ is independently selected from a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl group, and a $C_6$ to $C_{10}$ aryl group; $R^2$ is selected from a linear or branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; m is 1 or 2; n is 0, 1, or 2; p is 0, 1 or 2; and the sum of (m+n+p) is less than 4 and wherein $R^2$ and $R^3$ are linked to form a ring or $R^2$ and $R^3$ are not linked to form a ring; and providing a nitrogen-containing source into the reactor to at least partially react with the at least one organoaminosilane precursor and deposit a dielectric film onto the one or more substrates. In certain embodiments of the CVD method, the reactor is maintained at a pressure ranging from 100 mTorr to 600 mTorr during the introducing step.

As previously mentioned, the process described herein can be used to deposit a film using more than one precursor such as the halogenated organoaminosilane having Formula I described herein with an additional precursor such as a non-halogenated organoaminosilane precursor having Formula III described herein, a silicon-containing precursor such as those described herein, and/or a chlorosilane (such as, but not limited to, monochlorosilane (MCS), dichlorosilane (DCS), trichlorosilane or tetrachlorosilane), and/or alkylchlorosilane (such as, but not limited to, methylchlorosilane, ethylchlorosilane, methyldichlorosilane, ethyldichlorosilane). In these embodiments, the one or more precursors are described as a first precursor, a second precursor, a third precursor, etc. depending upon the number of different precursors used. The process can be used, for example, in a cyclic chemical vapor deposition or an atomic layer deposition. In these or other embodiments, the precursors can be introduced in a variety of ways (e.g., a) introduce first precursor; b) purge; c) introduce second precursor; d) purge; e) introduce third precursor; f) purge, etc., or, alternatively, a) introduce first precursor; b) purge; c) introduce second precursor; d) purge; e) introduce second precursor; etc.) In one particular embodiment, there is provided a process to deposit silicon oxide film or a silicon, carbon, and oxide film comprising the following steps:

a). Contacting vapors generated from a first precursor with a heated substrate to chemically sorb the first precursor on the heated substrate;

b). Purging away any unsorbed precursors;

c). Introducing an oxygen source on the heated substrate to react with the sorbed first precursor;

d). Purging away any unreacted oxygen source;

e). Contacting vapors generated from a second precursor which is different from the first precursor with a heated substrate to chemically sorb the second precursor on the heated substrate;

f). Purging away any unsorbed precursors;

g). Introducing an oxygen source on the heated substrate to react with the sorbed first and second precursors; and h) Purging away any unreacted oxygen source
wherein steps a). through h). are repeated until a desired thickness has been reached.

In a yet another embodiment of the process described herein, there is provided a method of depositing a silicon nitride or silicon carbonitride film comprising the following steps:

a). Contacting vapors generated from a first precursor with a heated substrate to chemically sorb the first precursors on the heated substrate;

b). Purging away any unsorbed first precursors;

c). Introducing a nitrogen source on the heated substrate to react with the sorbed first precursor;

d). Purging away any unreacted nitrogen source;

e). Contacting vapors generated from a second precursor which is different from the first with a heated substrate to chemically sorb the second precursor on the heated substrate;

f). Purging away any unsorbed second precursors;

g). Introducing a nitrogen source on the heated substrate to react with the sorbed second precursor; and h). Purging away any unreacted nitrogen source
wherein steps a) through h) are repeated until a desired thickness has been reached.

In a further embodiment, described herein is a process is deposit silicon-containing films employing cyclic chemical vapor deposition (CCVD) or atomic layer deposition (ALD) techniques such as, but not limited to, plasma enhanced ALD (PEALD) or plasma enhanced CCVD (PECCVD) process. In these embodiments, the deposition temperature may be relatively high, or from about 500 to 800° C., to control the specifications of film properties required in certain semiconductor applications. In one particular embodiment, the process comprises the following steps: contacting vapors generated from a halogenated organoaminosilane having Formula I with a heated substrate to chemically sorb the precursors on the heated substrate; purging away any unsorbed precursors; introducing a reducing agent to reduce the sorbed precursors; and purging away any unreacted reducing agent.

In certain embodiments, the halogenated organoaminosilane precursors having Formula I described herein can also be used a dopant for metal containing films, such as but not limited to, metal oxide films or metal nitride films. In these embodiments, the metal containing film is deposited using an ALD or CVD process such as those processes described herein using metal alkoxide, metal amide, or volatile organometallic precursors. Examples of suitable metal alkoxide precursors that may be used with the method disclosed herein include, but are not limited to, group 3 to 6 metal alkoxide, group 3 to 6 metal complexes having both alkoxy and alkyl substituted cyclopentadienyl ligands, group 3 to 6 metal complexes having both alkoxy and alkyl substituted pyrrolyl ligands, group 3 to 6 metal complexes having both alkoxy and diketonate ligands; group 3 to 6 metal complexes having both alkoxy and ketoester ligands; Examples of suitable metal amide precursors that may be used with the method disclosed herein include, but are not limited to, tetrakis(dimethylamino)zirconium (TDMAZ), tetrakis(diethylamino)zirconium (TDEAZ), tetrakis(ethylmethylamino)zirconium (TEMAZ), tetrakis(dimethylamino)hafnium (TDMAH), tetrakis(diethylamino)hafnium (TDEAH), and tetrakis(ethylmethylamino) hafnium (TEMAH), tetrakis(dimethylamino)titanium (TDMAT), tetrakis(diethylamino)titanium (TDEAT), tetrakis(ethylmethylamino)titanium (TEMAT), tert-butylimino tri(diethylamino)tantalum (TBTDET), tert-butylimino tri(dimethylamino)tantalum (TBTDMT), tert-butylimino tri(ethylmethylamino)tantalum (TBTEMT), ethylimino tri(diethylamino)tantalum (EITDET), ethylimino tri(dimethylamino)tantalum (EITDMT), ethylimino tri(ethylmethylamino)tantalum (EITEMT), tert-amylimino tri(dimethylamino)tantalum (TAIMAT), tert-amylimino tri(diethylamino)tantalum, pentakis(dimethylamino)tantalum, tert-amylimino tri(ethylmethylamino)tantalum, bis(tert-butylimino)bis(dimethylamino)tungsten (BTBMW), bis(tert-butylimino)bis(diethylamino)tungsten, bis(tert-butylimino) bis(ethylmethylamino)tungsten, and combinations thereof. Examples of suitable organometallic precursors that may be used with the method disclosed herein include, but are not limited to, group 3 metal cyclopentadienyls or alkyl cyclopentadienyls. Exemplary Group 3 to 6 metal herein include, but not limited to, Y, La, Ce, Pr, Nd, Sm, Eu, Gd, Tb, Dy, Er, Yb, Lu, Ti, Hf, Zr, V, Nb, Ta, Cr, Mo, and W. Other volatile organometallic precursors include, but are not limited to, metal alkyl precursors such as without limitation triethylaluminum (TEA), trimethylaluminum (TMA).

In certain embodiments, the halogenated organoaminosilanes can be used in a liquid-based deposition or film formation method such as, but not limited to, spin-on, dip coat, aerosol, ink jet, screen printing or spray applications. In embodiments where the silicon film is formed through a liquid-based deposition, the composite film is formed from a composition that comprises, inter alia, at least one silicon-containing precursor such as the halogenated organoaminosilane having Formula I described herein as a silica source, a catalyst, and water. The composition may further comprise a solvent and a surfactant. In brief, dispensing the composition onto a substrate and evaporating the solvent and water can form the film. The surfactant, remaining solvent and water are generally removed by exposing the coated substrate to one or more energy sources and for a time sufficient to produce the silicon-containing film. In some instances, the film may be pre-heated to substantially complete the hydrolysis of the silica source, continue the crosslinking process, and drive off any remaining solvent, if present, from the film.

Besides the halogenated organoaminosilane having Formula I described herein, another example of a silica source may include compounds that produce a Si—H bond upon removal of the pore-forming material.

Still further examples of the source are found in the non-hydrolytic chemistry methods described, for example, in the references Hay et al., "Synthesis of Organic-Inorganic Hybrids via the Non-hydrolytic Sol-Gel Process", Chem. Mater., 13, 3396-3403 (2001) or Hay, et al., "A Versatile Route to Organically-Modified Silicas and Porous Silicas via the Non-Hydrolytic Sol-Gel Process", J. Mater. Chem., 10, 1811-1818 (2000).

Yet another example of the silica source may include colloidal silica, fumed silica, or silicic acid starting materials.

Still other examples of silica sources include silsesquioxanes such as hydrogen silsesquioxanes (HSQ, $HSiO_{1.5}$) and methyl silsesquioxanes (MSQ, $RSiO_{1.5}$ where R is a methyl group).

In certain embodiments, the silica source may be added to the mixture as the product of hydrolysis and condensation. Hydrolysis and condensation of the silica source occurs by adding water and a catalyst to a solvent and adding the silica source at a time, intermittently or continuously, and conducting hydrolysis and condensation reactions while stirring the mixture at a temperature range generally from −30 to 100° C., preferably from 20 to 100° C., for 0 to 24 hours. The composition can be regulated to provide a desired solid content by conducting concentration or dilution with the solvent in each step of the preparation. Further, the silica source may be a compound that generates acetic acid when hydrolyzed.

The hydrolysis and condensation of the silica source can occur at any point during the formation of the film, i.e., before adding to the mixture, after adding to the mixture, prior to, and/or during exposure to at least one energy source, etc. For example, in certain embodiments, the at least one silica source is combined with the solvent, water, and surfactant in a vessel and the catalyst is gradually added into the vessel and mixed. It is envisioned that a variety of different orders of addition to the mixture can be used without departing from the spirit of the present invention.

The catalyst suitable for the present invention includes any organic or inorganic acid or base that can catalyze the hydrolysis of substitutents from the silica source in the presence of water, and/or the condensation of two silica sources to form a Si—O—Si bridge. The catalyst can be an organic base such as, but not limited to, quaternary ammonium salts and hydroxides, such as ammonium or tetramethylammonium, amines such as primary, secondary, and tertiary amines, and amine oxides. The catalyst can also be an acid such as, but not limited to, nitric acid, maleic, oxalic, acetic, formic, glycolic, glyoxalic acid, or mixtures thereof. In preferred embodiments, the catalyst comprises nitric acid.

Solvents that are suitable for the use in the present invention may include any solvents that exhibit solubility with the reagents. Solvents can be, for example, alcohol solvents, ketone solvents, amide solvents, or ester solvents. In certain embodiments the solvents may be a supercritical fluid such as carbon dioxide, fluorocarbons, sulfur hexafluoride, alkanes, and other suitable multi-component mixtures, etc. In certain embodiments, one or more solvents used in the present invention have relatively low boiling points, i.e., below 160° C. These solvents include, but are not limited to, tetrahydrofuran, acetone, 1,4-dioxane, 1,3-dioxolane, ethyl acetate, and methyl ethyl ketone. Other solvents, that can be used in the present invention but have boiling points above 160° C., include dimethylformamide, dimethylacetamide, N-methylpyrrolidone, ethylene carbonate, propylene carbonate, glycerol and derivatives, naphthalene and substituted versions, acetic acid anyhydride, propionic acid and propionic acid anhydride, dimethyl sulfone, benzophenone, diphenyl sulfone, phenol, m-cresol, dimethyl sulfoxide, diphenyl ether, terphenyl, and the like. Preferred solvents include propylene glycol propyl ether (PGPE), 3-heptanol, 2-methyl-1-pentanol, 5-methyl-2-hexanol, 3-hexanol, 2-heptano, 2-hexanol, 2,3-dimethyl-3-pentanol, propylene glycol methyl ether acetate (PGMEA), ethylene glycol n-butyl ether, propylene glycol n-butyl ether (PGBE), 1-butoxy-2-propanol, 2-methyl-3-pentanol, 2-methoxyethyl acetate, 2-butoxyethanol, 2-ethoxyethyl acetoacetate, 1-pentanol, and propylene glycol methyl ether. Still further exemplary solvents include lactates, pyruvates, and diols. Further exemplary solvents include those solvents listed in EP 1,127,929. The solvents enumerated above may be used alone or in combination of two or more solvents.

In certain embodiments, the reagents within the composition react to form a condensed flowable film on the substrate. This film flows into the gap to fill the gap with the dielectric material. The film is then converted to a solid dielectric material by one or more of various techniques including a thermal anneal, ultraviolet (UV) exposure, microwave exposure, or exposure to an oxidizing plasma. According to certain embodiments, the film is converted to the solid material by mechanisms including (but not limited to) cross-linking the precursor to produce the solid material and/or removal of hydrogen (—H), hydroxyl (—OH) or water ($H_2O$) groups. In a particular embodiment, an inductively-coupled plasma is used to convert the film.

In certain embodiments, the resultant dielectric films or coatings can be exposed to a post-deposition treatment such as, but not limited to, a plasma treatment, chemical treatment, ultraviolet light exposure, electron beam exposure, and/or other treatments to affect one or more properties of the film.

In certain embodiments, the dielectric films described herein have a dielectric constant of 6 or less. In these or other embodiments, the films can a dielectric constant of about 5 or below, or about 4 or below, or about 3.5 or below. However, it is envisioned that films having other dielectric constants (e.g., higher or lower) can be formed depending upon the desired end-use of the film. In one embodiment of the silicon containing or dielectric film that is formed using the organoaminosilane precursors and processes described herein has the formulation $Si_xO_yC_zN_vH_w$ wherein Si ranges from about 10% to about 40%; O ranges from about 0% to about 65%; C ranges from about 0% to about 75% or from about 0% to about 50%; N ranges from about 0% to about 75% or from about 0% to 50%; and H ranges from about 0% to about 50% atomic percent weight % wherein x+y+z+v+w=100 atomic weight percent, as determined for example, by XPS or other means. However, other embodiments of dielectric or silicon-containing films with different formulations can be made using the halogenated organoaminosilane precursors described herein.

As mentioned previously, the method described herein may be used to deposit a silicon-containing film on at least a portion of a substrate. Examples of suitable substrates include but are not limited to, silicon, $SiO_2$, $Si_3N_4$, OSG, FSG, silicon carbide, hydrogenated silicon carbide, silicon nitride, hydrogenated silicon nitride, silicon carbonitride, hydrogenated silicon carbonitride, boronitride, antireflective coatings, photoresists, organic polymers, porous organic and inorganic materials, metals such as copper and aluminum, and diffusion barrier layers such as but not limited to TiN, Ti(C)N, TaN, Ta(C)N, Ta, W, or WN. The films are compatible with a variety of subsequent processing steps such as, for example, chemical mechanical planarization (CMP) and anisotropic etching processes.

The deposited films have applications, which include, but are not limited to, computer chips, optical devices, magnetic information storages, coatings on a supporting material or substrate, microelectromechanical systems (MEMS), nano-electromechanical systems, thin film transistor (TFT), and liquid crystal displays (LCD).

In the claims, letters are used to identify claimed steps (e.g. (a), (b), and (c)). These letters are used to aid in referring to the method steps and are not intended to indicate the order in which claimed steps are performed, unless and only to the extent that such order is specifically recited in the claims.

The following examples illustrate the method for preparing halogenated organoaminosilane precursors described herein as well as deposited silicon-containing films described herein and are not intended to limit it in any way.

EXAMPLES

Example 1

Synthesis of 2,6-Dimethylpiperidinochlorosilane

In a 2000 ml 3-necked round bottom flask equipped with mechanical stirror and an addition funnel, 1000 ml hexane was added. With the flask was cooled to –20° C. using a dry ice IPA cold bath, 101 g (1.0 mol) dichlorosilane was condensed and dissolved into hexane. With stirring, a mixture of 113 g (1.0 mol) 2,6-dimethylpiperidine and 111 g (1.1 mol) triethylamine was added dropwise to the flask. After the addition was complete, the reaction mixture was stirred at –20° C. for 1 hour, and then let warming up to room temperature. A salt byproduct precipitate of $HCl.Et_3N$ was removed by vacuum filtration in a glove bag purging with $N_2$ to prevent the product reacting with the moisture in the air. A GC/MS analysis on the filtrate confirmed the product 2,6-dimethylpiperidinochlorosilane, showing the product with a molecular ion mass of 177 and supporting mass fragment of mass M —$CH_3$ of 162. The solvent hexane was removed by distillation and the product was separated by vacuum distillation. The boiling point was 60° C. at 10 torr. The yield was 66%.

Example 2

Alternative Synthetic Route for 2,6-Dimethylpiperidinochlorosilane

To a solution of 7.55 g (66.68 mmol) cis-2,6-dimethylpiperidine in 50 mL of THF at –78° C. was drop-wise added 28.00 mL (70.02 mmol) of a 2.5M solution of n-butyllithium in hexanes. A precipitate evolved and the reaction mixture was warmed to room temperature while stirring. After one hour this mixture was added drop-wise to a solution of 6.74 g (66.68 mmol) dichlorosilane in 30 mL xylenes and 70 mL hexanes at –40° C. and a light gray precipitate formed. The reaction mixture was stirred for 16 hours after which it was decanted from the evolved solid and subjected to distillation at ambient pressure to remove volatiles. 3.16 g of desired product was isolated with a yield of 27%. The product was confirmed by GC/MS analysis as 2,6-Dimethylpiperidinochlorosilane.

Example 3

Synthesis of 2,6-Dimethylpiperidinodichlorosilane

A synthesis of 2,6-dimethylpiperidinodichlorosilane was produced by mixing a mole ratio of 1 part 2,6-dimethylpiperidine to 1 part triethylamine to 1.1 part trichlorosilane in a 70% by weight hexane solution. An excess amount of trichlorosilane was needed to prevent the formation of bis(2,6-dimethylpiperindo)chlorosilane. A salt byproduct precipitate of HCl.Et$_3$N was removed by vacuum filtration in a glove bag purging with N$_2$ to prevent the product reacting with the moisture in the air. A GC/MS analysis (which is shown in FIG. 1) on the filtrate confirmed the product 2,6-dimethylpiperidinodichlorosilane was produced, resulting a mass of 211 and supporting mass fragment of mass —CH$_3$ of 196. After vacuum filtration, the gross amount of hexane was removed be by simple distillation in the first step. The second step used the vacuum distillation technique, which the product was collected. A boiling points were determined from the vacuum distillation is 93° C. at 18 torr, and 66° C. at 5 torr. The yield was 64%.

Example 4

Atomic Layer Deposition of Silicon-containing Films

Atomic layer depositions of silicon-containing films were conducted using the following precursor: 2,6-dimethylpiperidinochlorosilane. The depositions were performed on a laboratory scale ALD processing tool. All gases (e.g., purge and reactant gas or precursor and oxygen source) were preheated to 100° C. prior to entering the deposition zone. Gases and precursor flow rates were controlled with ALD diaphragm valves having high speed actuation. The substrates used in the deposition were 12 inch length silicon strips having thermocouple attached on a sample holder to confirm the substrate temperature. Depositions were performed using ozone as the oxygen source gas and the process parameters of the depositions are provided in Table II:

TABLE II

Process for Atomic Layer Deposition of Silicon-containing Films with Ozone

| Step a) | 6 sec | Chamber evacuation | <100 mT | Prepare the reactor for the precursor dose |
| Step b) | Variable | Dose halogenated organoaminosilane Precursor | | Reactor pressure typically <1 Torr during dose |
| Step c) | 6 sec | Nitrogen purge of reactor | Flow 1.5 slpm N$_2$ | Purges out unreacted chemical from reactor |
| Step d) | 6 sec | Chamber evacuation | <100 mT | Prepare the reactor for the organoaminosilane precursor dose |
| Step e) | 2 sec | Dose Ozone | | ozone at 18-20% wt post generator, P = <8 Torr |

Steps b) to e) are repeated until a desired thickness is reached. The resultant silicon-containing films were characterized for deposition rate and refractive index. Thickness and refractive indices of the films was measured using a FilmTek 2000SE ellipsometer by fitting the reflection data from the film to a pre-set physical model (e.g., the Lorentz Oscillator model). Film composition was analyzed with X-Ray Photoelectron Spectroscopy (XPS) technique. The X-ray Photoelectron Spectroscopy experiments are performed on a PHI 5000VersaProbe Spectrometer equipped with Multiple Channels Plates (MCD) and a focused Al monochromatic X-ray source. Film compositions were measured at 100 Å into the film to remove adventitious carbon signal. The measured film composition omitted hydrogen, as it is not detectable with XPS, and normalized to 100%.

X-ray Reflectometry (XRR) was performed on all samples to determine film density. Samples were scanned over the range 0.2≤2≤0.65 using a step size of 0.001 and a count time of 1s/step. Data were analyzed using a two-layer model with the substrate defined as Si and film as silicon oxide.

Silicon oxide films were formed using 2,6-dimethylpiperidinochlorosilane at various substrate temperature from 150 to 300° C. at one second precursor dose as summarized in Table III:

TABLE III

Summary of Process Parameters and Results for 2,6-dimethylpiperidinochlorosilane

| No. | Wafer temperature (Celcius) | Precursor dose (seconds) | Deposition Rate (Å/cycle) |
| --- | --- | --- | --- |
| 1 | 50 | 1 | 0.15 |
| 2 | 150 | 1 | 0.22 |
| 3 | 300 | 1 | 0.55 |

Silicon oxide films were formed using 2,6-dimethylpiperidinochlorosilane at substrate temperature of 300° C. at variable precursor doses as summarized in Table IV:

TABLE IV

Summary of Process Parameters and Results for 2,6-dimethylpiperidinochlorosilane

| No. | Wafer temperature (Celcius) | Precursor dose (seconds) | Deposition Rate (Å/cycle) | Refractive index |
| --- | --- | --- | --- | --- |
| 1 | 300 | 0.5 | 0.43 | 1.46 |
| 2 | 300 | 1 | 0.55 | 1.49 |
| 3 | 300 | 2 | 0.60 | 1.48 |
| 4 | 300 | 4 | 0.50 | 1.51 |

Silicon oxide deposition shows deposition rate saturation with increasing precursor dose, demonstrating a self-limited atomic layer deposition (ALD) like behavior. Deposited films have 33 at. % of Si and 67 at. % 0, as measured by X-ray photospectroscopy (XPS). No carbon, nitrogen and chlorine were detected in the films. Film density is 1.9±0.05 g/cc.

The invention claimed is:

1. A method for forming a dielectric film on at least one surface of a substrate by a deposition process chosen from a chemical vapor deposition process and an atomic layer deposition process, the method comprising:

providing the at least one surface of the substrate in a reaction chamber;

introducing at least one halogenated organoaminosilane precursor having the following Formula I:

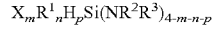

$$X_m R^1_n H_p Si(NR^2R^3)_{4-m-n-p} \quad\quad I$$

wherein X is a halide selected from the group consisting of Cl, Br, I; R$^1$ is independently selected from a linear or branched C$_1$ to C$_{10}$ alkyl group, a C$_2$ to C$_{12}$ alkenyl group, a C$_2$ to C$_{12}$ alkynyl group, a C$_4$ to C$_{10}$ cyclic alkyl, and a C$_6$ to C$_{10}$ aryl group; R$^2$ is selected from a linear or branched C$_1$ to C$_{10}$ alkyl group, a C$_3$ to C$_{12}$ alkenyl group, a C$_3$ to C$_{12}$ alkynyl group, a C$_4$ to C$_{10}$ cyclic alkyl group, and a C$_6$ to C$_{10}$ aryl group; R$^3$ is selected from a branched C$_3$ to C$_{10}$ alkyl group, a C$_3$ to C$_{12}$ alkenyl group, a C$_3$ to C$_{12}$ alkynyl group, a C$_4$ to C$_{10}$ cyclic alkyl group, and a C$_6$ to C$_{10}$ aryl group; m is 1 or 2; n is 0, 1, or 2; p is 0, 1 or 2; and the sum of (m+n+p) is less than 4 and wherein R$^2$ and R$^3$ are linked to form a ring;

introducing a nitrogen-containing source into the reaction chamber wherein the at least one halogenated organoaminosilane precursor and the nitrogen-containing source react to provide the dielectric film on the at least one surface wherein the at least one organoaminosilane precursor is selected from the group consisting of 2,6-dimethylpiperidinodichlorosilane, 2,6-dimethylpiperidinochlorosilane, cyclohexylmethylaminochlorosilane, cyclohexylethylaminochlorosilane, and cyclohexyl-iso-propylaminochlorosilane.

2. The method of claim 1 wherein the at least one organoaminosilane precursor comprises 2,6-dimethylpiperidinodichlorosilane.

3. The method of claim 1 wherein the at least one organoaminosilane precursor comprises 2,6-dimethylpiperidinochlorosilane.

4. The method of claim 1 wherein the nitrogen-containing source is selected from the group consisting of ammonia, hydrazine, monoalkylhydrazine, dialkylhydrazine, nitrogen/hydrogen, ammonia plasma, nitrogen plasma, nitrogen/hydrogen plasma, and mixtures thereof.

5. The method of claim 1 wherein the dielectric film is selected from the group consisting of silicon nitride and silicon carbonitride.

6. A method of forming a dielectric film via an atomic layer deposition (ALD) process, the method comprising the steps of:
a. providing a substrate in an ALD reactor;
b. providing in the ALD reactor an at least one halogenated organoaminosilane precursor having the following Formula I:

$$X_m R^1{}_n H_p Si(NR^2R^3)_{4-m-n-p} \qquad I$$

wherein X is a halide selected from the group consisting of Cl, Br, I; $R^1$ is independently selected from a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl, and a $C_6$ to $C_{10}$ aryl group; $R^2$ is selected from a linear or branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_1$ to $C_{10}$ alkyl, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; m is 1 or 2; n is 0, 1, or 2; p is 0, 1 or 2; and the sum of (m+n+p) is less than 4 and wherein $R^2$ and $R^3$ are linked to form a ring or $R^2$ and $R^3$ are not linked to form a ring;
c. purging the ALD reactor with an inert gas;
d. providing a nitrogen-containing source in the ALD reactor;
e. purging the ALD reactor with an inert gas; and
repeating the steps b through e until a desired thickness of the dielectric film is obtained wherein the at least one halogenated organoaminosilane precursor is selected from the group consisting of 2,6-dimethylpiperidinodichlorosilane, 2,6-dimethylpiperidinochlorosilane, cyclohexylmethylaminochlorosilane, cyclohexylethylaminochlorosilane, and cyclohexyl-iso-propylaminochlorosilane.

7. The method of claim 6 wherein the at least one halogenated organoaminosilane precursor comprises 2,6-dimethylpiperidinodichlorosilane.

8. The method of claim 6 wherein the at least one halogenated organoaminosilane precursor comprises 2,6-dimethylpiperidinochlorosilane.

9. The method of claim 6 wherein the nitrogen-containing source is selected from the group consisting of ammonia, hydrazine, monoalkylhydrazine, dialkylhydrazine, nitrogen, nitrogen/hydrogen, ammonia plasma, nitrogen plasma, nitrogen/hydrogen plasma, and mixtures thereof.

10. The method of claim 6 wherein the dielectric film is selected from the group consisting of silicon nitride and silicon carbonitride.

11. A method of forming a dielectric film onto at least a surface of a substrate using a plasma enhanced atomic layer deposition (PEALD) process, the method comprising:
a. providing a substrate in an ALD reactor;
b. providing in the ALD reactor an at least one halogenated organoaminosilane precursor having the following Formula I:

$$X_m R^1{}_n H_p Si(NR^2R^3)_{4-m-n-p} \qquad I$$

wherein X is a halide selected from the group consisting of Cl, Br, I; $R^1$ is independently selected from a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl, and a $C_6$ to $C_{10}$ aryl group; $R^2$ is selected from a linear or branched $C_1$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; m is 1 or 2; n is 0, 1, or 2; p is 0, 1 or 2; and the sum of (m+n+p) is less than 4 and wherein $R^2$ and $R^3$ are linked to form a ring or $R^2$ and $R^3$ are not linked to form a ring;
c. purging the ALD reactor with an inert gas;
d. providing a plasma nitrogen-containing source in the ALD reactor;
e. purging the ALD reactor with an inert gas; and
repeating the steps b through e until a desired thickness of the dielectric film is obtained wherein the at least one halogenated organoaminosilane precursor is selected from the group consisting of 2,6-dimethylpiperidinodichlorosilane, 2,6-dimethylpiperidinochlorosilane, cyclohexylmethylaminochlorosilane, cyclohexylethylaminochlorosilane, and cyclohexyl-iso-propylaminochlorosilane.

12. The method of claim 11 wherein the at least one halogenated organoaminosilane precursor comprises 2,6-dimethylpiperidinodichlorosilane.

13. The method of claim 11 wherein the at least one halogenated organoaminosilane precursor comprises 2,6-dimethylpiperidinochlorosilane.

14. The method of claim 11 wherein the nitrogen-containing source is selected from the group consisting of ammonia, hydrazine, monoalkylhydrazine, dialkylhydrazine, nitrogen, nitrogen/hydrogen, ammonia plasma, nitrogen plasma, nitrogen/hydrogen plasma, and mixtures thereof.

15. The method of claim 11 wherein the dielectric film is selected from the group consisting of silicon nitride and silicon carbonitride.

16. A method for forming a silicon oxide film on a substrate comprising:
reacting an oxidizing agent with a precursor comprising a halogenated organoaminosilane represented by the following Formula I:

$$X_m R^1{}_n H_p Si(NR^2R^3)_{4-m-n-p} \qquad I$$

wherein X is a halide selected from the group consisting of Cl, Br, I; $R^1$ is independently selected from a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl, and a $C_6$ to $C_{10}$ aryl group; $R^2$ is selected from a linear or branched $C_1$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; m is 1 or 2; n is 0, 1, or 2; p is 0, 1 or 2; and the sum of (m+n+p) is less than 4 and wherein $R^2$ and $R^3$ are linked to form a ring in a vapor deposition process to form the silicon oxide film on the substrate wherein the at least one halogenated organoaminosilane precursor is selected from the group consisting of 2,6-dimethylpiperidinodichlorosilane, 2,6-dimethylpiperidinochlorosilane, cyclohexylmethylaminochlorosilane, cyclohexylethylaminochlorosilane, and cyclohexyl-iso-propylaminochlorosilane.

17. The method of claim 16 wherein the vapor deposition is at least one selected from the group consisting of at least one selected from chemical vapor deposition, low pressure vapor deposition, plasma enhanced chemical vapor deposition, cyclic chemical vapor deposition, plasma enhanced cyclic chemical vapor deposition, atomic layer deposition, and plasma enhanced atomic layer deposition.

18. The method of claim 16 wherein the at least one halogenated organoaminosilane precursor comprises 2,6-dimethylpiperidinodichlorosilane.

19. The method of claim 16 wherein the at least one halogenated organoaminosilane precursor comprises 2,6-dimethylpiperidinochlorosilane.

20. A method for forming a silicon oxide film on a substrate comprising:
forming via vapor deposition of the silicon oxide film on the substrate from a composition comprising at least one organoaminosilane precursor having the following Formula I:

$$X_m R^1_n H_p Si(NR^2R^3)_{4-m-n-p} \quad\quad I$$

wherein X is a halide selected from the group consisting of Cl, Br, I; $R^1$ is independently selected from a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl, and a $C_6$ to $C_{10}$ aryl group; $R^2$ is selected from a linear or branched $C_1$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; m is 1 or 2; n is 0, 1, or 2; p is 0, 1 or 2; and the sum of (m+n+p) is less than 4 and wherein $R^2$ and $R^3$ are linked to form a ring or $R^2$ and $R^3$ are not linked to form a ring and at least one oxidizing agent,
wherein the vapor deposition is at least one selected from chemical vapor deposition, low pressure vapor deposition, plasma enhanced chemical vapor deposition, cyclic chemical vapor deposition, plasma enhanced cyclic chemical vapor deposition, atomic layer deposition, and plasma enhanced atomic layer deposition; and wherein the at least one halogenated organoaminosilane precursor is selected from the group consisting of 2,6-dimethylpiperidinodichlorosilane, 2,6-dimethylpiperidinochlorosilane, cyclohexylmethylaminochlorosilane, cyclohexylethylaminochlorosilane, and cyclohexyl-iso-propylaminochlorosilane.

21. The method of claim 20 wherein the at least one halogenated organoaminosilane precursor comprises 2,6-dimethylpiperidinodichlorosilane.

22. The method of claim 20 wherein the at least one halogenated organoaminosilane precursor comprises 2,6-dimethylpiperidinochlorosilane.

23. A method for forming a silicon oxide film on a substrate comprising:
introducing a halogenated organoaminosilane represented by the following Formula I:

$$X_m R^1_n H_p Si(NR^2R^3)_{4-m-n-p} \quad\quad I$$

wherein X is a halide selected from the group consisting of Cl, Br, I; $R^1$ is independently selected from a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl, and a $C_6$ to $C_{10}$ aryl group; $R^2$ is selected from a linear or branched $C_1$ to $C_{10}$ alkyl, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; m is 1 or 2; n is 0, 1, or 2; p is 0, 1 or 2; and the sum of (m+n+p) is less than 4 and wherein $R^2$ and $R^3$ are linked to form a ring or $R^2$ and $R^3$ are not linked to form a ring into a reactor;
introducing at least one oxidizing agent into the reactor wherein the at least one oxidizing agent reacts with the organoaminosilane to provide the silicon oxide film on the substrate wherein the halogenated organoaminosilane is selected from the group consisting of 2,6-dimethylpiperidinochlorosilane, 2,6-dimethylpiperidinodichlorosilane, dicyclohexylaminochlorosilane, cyclohexylmethylaminochlorosilane, cyclohexylethylaminochlorosilane, cyclohexyl-iso-propylaminochlorosilane, N-(chlorosilyl)perhydroguinoline, phenylallylaminochlorosilane, m-tolylmethylaminochlorosilane, N-(chlorosilyl)carbazole, N-(chlorosilyl)-tetrahydroguinoline, N-(chlorosilyl)indole, N-(chlorosilyl)-2-methylindole, N-(chlorosilyl)-3-methylindole, and N-(chlorosilyl)-1,2,3,4-Tetrahydro-2-methylguinoline.

24. A method for forming a silicon oxide film on a substrate wherein the film comprises a thickness, the method comprising:
a. introducing an at least one halogenated organoaminosilane represented following Formula I:

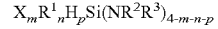

$$X_m R^1_n H_p Si(NR^2R^3)_{4-m-n-p} \quad\quad I$$

wherein X is a halide selected from the group consisting of Cl, Br, I; $R^1$ is independently selected from a linear or branched $C_1$ to $C_{10}$ alkyl group, a $C_2$ to $C_{12}$ alkenyl group, a $C_2$ to $C_{12}$ alkynyl group, a $C_4$ to $C_{10}$ cyclic alkyl, and a $C_6$ to $C_{10}$ aryl group; $R^2$ is selected from a linear or branched $C_1$ to $C_{10}$ alkyl, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; m is 1 or 2; n is 0, 1, or 2; p is 0, 1 or 2; and the sum of (m+n+p) is less than 4 and wherein $R^2$ and $R^3$ are linked to form a ring into a deposition chamber;
b. chemisorbing the at least one halogenated organoaminosilane precursor onto the substrate;
c. purging away the unreacted at least one halogenated organoaminosilane precursor using a purge gas;
d. providing an oxygen source to the halogenated organoaminosilane precursor onto the heated substrate to react with the sorbed at least one halogenated organoaminosilaneprecursor; and e. optionally purging away any unreacted oxygen source;
wherein the at least one organoaminosilane precursor is selected from the group consisting of 2,6-dimethylpiperidinodichlorosilane, 2,6-dimethylpiperidinochlorosilane, cyclohexylmethylaminochlorosilane, cyclohexylethylaminochlorosilane, and cyclohexyl-iso-propylaminochlorosilane.

25. The method of claim 24 wherein steps a. through d. and optional step e. are repeated until the thickness of film is established.

26. The method of claim 24 wherein the at least one halogenated organoaminosilane precursor comprises 2,6-dimethylpiperidinodichlorosilane.

27. The method of claim 24 wherein the at least one halogenated organoaminosilane precursor comprises 2,6-dimethylpiperidinochlorosilane.

28. The method of claim 24 is an atomic layer deposition process.

29. The method of claim 24 is a plasma enhanced cyclic chemical vapor deposition process.

30. A halogenated organoaminosilane precursor selected from the group consisting of 2,6-dimethylpiperidinochlorosilane, 2,6-dimethylpiperidinodichlorosilane, dicyclohexylaminochlorosilane, cyclohexylmethylaminochlorosilane, cyclohexylethylaminochlorosilane, cyclohexyl-iso-propylaminochlorosilane, N-(chlorosilyl)perhydroquinoline, phenylallylaminochlorosilane, m-tolylmethylaminochlorosilane, N-(chlorosilyl)carbazole, N-(chlorosilyl)-tetrahydroquinoline, N-(chlorosilyl)indole, N-(chlorosilyl)-2-methylindole, N-(chlorosilyl)-3-methylindole, and N-(chlorosilyl)-1,2,3,4-Tetrahydro-2-methylquinoline.

31. A method for forming a silicon-containing film on at least one surface of a substrate by a deposition process chosen from a chemical vapor deposition process and an atomic layer deposition process, the method comprising:
providing the at least one surface of the substrate in a reaction chamber;
introducing at least one halogenated organoaminosilane comprising at least one selected from the group consisting of 2,6dimethylpiperidinochlorosilane, 2,6-dimethylpiperidinodichlorosilane, dicyclohexylaminochlorosilane, cyclohexylmethylaminochlorosilane, cyclohexylethylaminochlorosilane, cyclohexyl-iso-propylaminochlorosilane, N-(chlorosilyl)perhydroquinoline, phenylallylaminochlorosilane, m-tolylmethylaminochlorosilane, N-(chlorosilyl)carbazole, N-(chlorosilyl)-tetrahydroquinoline, N-(chlorosilyl)indole, N-(chlorosilyl)-2-methylindole, N-(chlorosilyl)-3-methylindole, N-(chlorosilyl)-1,2,3,4-Tetrahydro-2-methylquinoline, and combinations thereof and
wherein the at least one halogenated organoaminosilane reacts to provide the film on the at least one surface.

32. A method for forming a silicon-containing film on at least one surface of a substrate by a deposition process chosen from a chemical vapor deposition process and an atomic layer deposition process, the method comprising:
providing the at least one surface of the substrate in a reaction chamber;
introducing at least one halogenated organoaminosilane precursor having the following formula:

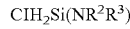

wherein $R^2$ is selected from a linear or branched $C_1$ to $C_{10}$ alkyl group, a $C_3$ to $C_{12}$ alkenyl group, a $C_3$ to $C_{12}$ alkynyl group, a $C_4$ to $C_{10}$ cyclic alkyl group, and a $C_6$ to $C_{10}$ aryl group; $R^3$ is selected from a branched $C_3$ to $C_{10}$ alkyl group, a $C_3$ to $C_{12}$ alkenyl group, a $C_3$ to $O_{12}$ alkynyl group, a $C_4$ to $C_{10}$ cyclic alkyl group, and a $C_6$ to $C_{10}$ aryl group; and wherein $R^2$ and $R^3$ can form a cyclic or alkyl substituted cyclic ring into the reaction chamber wherein the at least one halogenated organoaminosilane reacts to provide the film on the at least one surface.

33. The method of claim 32 wherein the at least one halogenated organoaminosilane precursor comprises at least one selected from the group consisting of di-iso-propylaminochlorosilane, di-sec-buylaminochlorosilane, di-iso-butylaminochlorosilane, iso-propylmethylaminochlorosilane, iso-propylethylaminochlorosilane, phenylethylaminochlorosilane, phenylmethylaminochlorosilane, m-tolylmethylaminochlorosilane, and combinations thereof.

34. A halogenated organoaminosilane precursor selected from the group consisting of di-iso-propylaminochlorosilane, di-sec-buylaminochlorosilane, di-sec-buylaminodichlorosilane, di-iso-butylaminochlorosilane, di-iso-butylaminodichlorosilane, cyclohexylmethylaminodichlorosilane, cyclohexylethylaminodichlorosilane, cyclohexyl-iso-propylaminodichlorosilane, isopropylmethylaminochlorosilane, isopropylethylaminochlorosilane, phenylmethylaminochlorosilane, phenylethylaminochlorosilane, phenylisopropylaminochlorosilane, iso-propylmethylaminochlorosilane, N-chlorosilyl-3-anilinopropionitrile, N-chlorosilyl-N-phenylglycinonitrile, phenylcyclohexylaminochlorosilane, N-(chlorosilyl)benzomorpholine, o-tolylethylaminochlorosilane, p-tolylethylaminochlorosilane m-tolylethylaminochlorosilane, p-tolylmethylaminochlorosilane, and o -tolylmethylaminochlorosilane.

35. A composition for depositing a dielectric film via a deposition process chosen from a chemical vapor deposition process and an atomic layer deposition process comprsing:
a) a halogenated organoaminosilane precursor selected from the group consisting of 2,6-dimethylpiperidinochlorosilane, 2,6-dimethylpiperidinodichlorosilane, di-iso-propylaminochlorosilane, di-iso-propylaminodichlorosilane, di-sec-buylaminochlorosilane, di-sec-buylaminodichlorosilane, Di-iso-butylaminochlorosilane, di-iso-butylaminodichlorosilane, cyclohexylmethylaminodichlorosilane, cyclohexylethylaminodichlorosilane, cyclohexyl-iso-propylaminodichlorosilane, isopropylmethylaminochlorosilane, isopropylethylaminochlorosilane, phenylmethylaminochlorosilane, phenylethylaminochlorosilane, phenylisopropylaminochlorosilane, iso-propylmethylaminochlorosilane, iso-propylethylaminochlorosilane, N-chlorosilyl-3-anilinopropionitrile, N-chlorosilyl-N-phenylglycinonitrile, phenylcyclohexylaminochlorosilane, N-(chlorosilyl)benzomorpholine, o-tolylethylaminochlorosilane, p-tolylethylaminochlorosilane, m-tolylethylaminochlorosilane, p-tolylmethylaminochlorosilane, and o-tolylmethylaminochlorosilane, and;
b) a solvent selected from the group consisting of an ether, a tertiary amine, a nitrile, an alkyl hydrocarbon, an aromatic hydrocarbon, a tertiary amino ether, or mixtures thereof.

36. A method for forming a silicon-containing film on at least one surface of a substrate by a deposition process chosen from a chemical vapor deposition process and an atomic layer deposition process, the method comprising:
providing the at least one surface of the substrate in a reaction chamber;
introducing at least one halogenated organoaminosilane comprising at least one selected from the group consisting of di-iso-propylaminochlorosilane, di-sec-buylaminochlorosilane, di-sec-buylaminodichlorosilane, di-iso-butylaminochlorosilane, di-iso-butylaminodichlorosilane, cyclohexylmethylaminodichlorosilane, cyclohexylethylaminodichlorosilane, cyclohexyl-iso-propylaminodichlorosilane, isopropylmethylaminochlorosilane, isopropylethylaminochlorosilane, phenylmethylaminochlorosilane, phenylethylaminochlorosilane, phenylisopropylaminochlorosilane, iso-propylmethylaminochlorosilane, iso-propylethylaminochlorosilane, N-chlorosilyl-3-anilinopropionitrile, N-chlorosilyl-N-phenylglycinonitrile, phenylcyclohexylaminochlorosilane, N-(chlorosilyl)benzomorpholine, o-tolylethylaminochlorosilane, p-tolylethylaminochlorosilane m-tolylethylaminochlorosilane, p-tolylmethylaminochlorosilane, and o-tolylmethylaminochlorosilane and wherein the at least one halogenated organoaminosilane reacts to provide the film on the at least one surface.

* * * * *

UNITED STATES PATENT AND TRADEMARK OFFICE
CERTIFICATE OF CORRECTION

PATENT NO.       : 8,993,072 B2                          Page 1 of 1
APPLICATION NO.  : 13/622117
DATED            : March 31, 2015
INVENTOR(S)      : Xiao et al.

It is certified that error appears in the above-identified patent and that said Letters Patent is hereby corrected as shown below:

In the Claims

Column 35, Line 67
In claim 32 delete the "0" and insert --C--

Column 36, Line 25
In claim 34 delete the word "N-chlorosilyI-3-anilinopropionitrile" and insert the word
--N-chlorosilyl-3-anilinopropionitrile--

Signed and Sealed this
Second Day of February, 2016

Michelle K. Lee
*Director of the United States Patent and Trademark Office*